(12) United States Patent
Diolez et al.

(10) Patent No.: US 7,705,155 B2
(45) Date of Patent: Apr. 27, 2010

(54) PROCESSES FOR THE PRODUCTION OF USEFUL INTERMEDIATES

(75) Inventors: Christian Diolez, Palaiseau (FR); Eric Manginot, Montfavet (FR); Rene Peters, Zürich (CH); Alain Rolland, Palaiseau (FR); Marc Veyrat, LePontet (FR)

(73) Assignee: Societe de Conseils de Recherches et D'Applications Scientifiques, Paris (FR)

( * ) Notice: Subject to any disclaimer, the term of this patent is extended or adjusted under 35 U.S.C. 154(b) by 0 days.

(21) Appl. No.: 11/689,152

(22) Filed: Mar. 21, 2007

(65) Prior Publication Data

US 2007/0167475 A1  Jul. 19, 2007
US 2009/0247563 A9  Oct. 1, 2009

Related U.S. Application Data

(63) Continuation of application No. PCT/IB2005/003032, filed on Sep. 20, 2005.

(30) Foreign Application Priority Data

Sep. 21, 2004 (EP) ................... 04022472
Feb. 4, 2005 (EP) ................... 05100781

(51) Int. Cl.
*C07D 213/64* (2006.01)
(52) U.S. Cl. ..................................... 546/301; 546/302

(58) Field of Classification Search ................ 546/302, 546/301, 51
See application file for complete search history.

(56) References Cited

U.S. PATENT DOCUMENTS 6,339,091 B1  1/2002  Bigg et al.
6,723,853 B2  4/2004  Curran et al.
7,012,079 B1  3/2006  Lavergne et al.

FOREIGN PATENT DOCUMENTS

WO  WO00/50427 A1  8/2000
WO  WO2006/033011 A1  3/2006

OTHER PUBLICATIONS

Peters et.al. "Practical Formal Total Syntheses of the Homocamptothecin Derivative and Anticancer Agent Diflomotecan via Asymmetric Acetate Aldol Additions to Pyridine Ketone Substrates", J. Org. Chem. 2006, 71, 7583-7595.*
Written Opinion for PCT/IB2005/003032.
Dongala et al.: "Synthese Asmetrique de Beta-Hydroxyacides par condensation aldolique." Tetrahedron Letters, vol. 50, pp. 4983-4986, 1973 (XP002363018).

* cited by examiner

*Primary Examiner*—Patricia L Morris
(74) *Attorney, Agent, or Firm*—Hunton & Williams LLP

(57) ABSTRACT

The present application relates to a new process for the asymmetric production of 3-(pyridin-4-yl)-3-hydroxy-pentanoic acid derivatives, which are useful intermediates in the manufacture of compounds that are known to show antiproliferative activity.

17 Claims, No Drawings

PROCESSES FOR THE PRODUCTION OF USEFUL INTERMEDIATES

CONTINUITY DATA

This application is a application continuation of PCT/IB2005/003032, filed on Sep. 20, 2005, which in turn claims priority to EP 05100781.3, filed on Feb. 4, 2005 and EP 04022472.7, filed on Sep. 21, 2004.

FIELD OF INVENTION

The present application relates to a new process for the production of 3-(pyridin-4-yl)-3-hydroxy-pentanoic acid derivatives.

In particular the present invention relates to a process for the production of the compounds of formula (I)

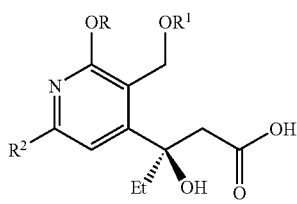
(I)

and pharmaceutically acceptable salts and esters thereof, comprising
a) reacting a compound of formula (II),

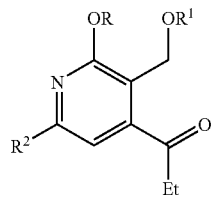
(II)

with a compound of formula (III),

(III)

and
b) further reaction in the presence of alkali- or earth alkali metal hydroxides to give the compounds of formula (I), wherein
R and $R^1$ are independently, alkyl or benzyl, which benzyl is optionally substituted by
one, two or three substituents independently selected from
—O-alkyl; alkyl and halogen; and
if R is alkyl, $R^1$ in formula (I) is also hydrogen or silyl, and $R^1$ in formula (II) is also silyl;
$R^2$ is hydrogen or halogen;

X is

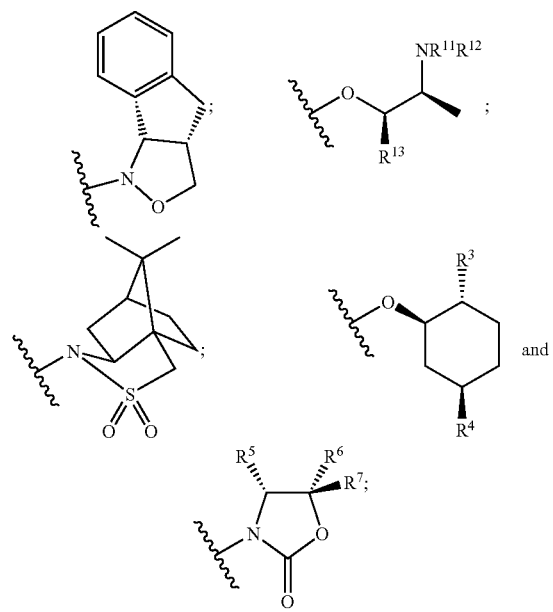

$R^3$ and $R^4$ are independently selected from hydrogen, phenyl, alkyl and —$C(CH_3)_2$-phenyl;
$R^5$ is phenyl, benzyl or alkyl;
$R^6$ is hydrogen, alkyl or phenyl; and
$R^7$ is hydrogen, methyl or phenyl; or alternatively
$R^5$ and $R^6$, together with the carbon atoms to which they are attached form an indan-moiety and $R^7$ is hydrogen;
$R^{11}$ and $R^{12}$ are independently alkyl, cycloalkyl, benzyl or phenyl; and
$R^{13}$ is phenyl or alkyl.

In a preferred embodiment, the present invention relates to a process for the production of the compounds of formula (I)

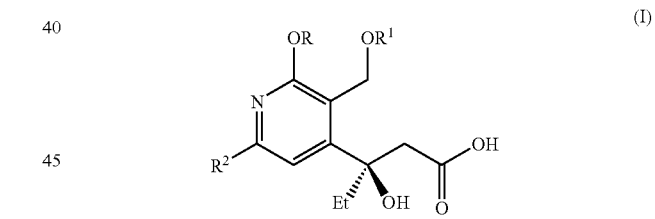
(I)

and pharmaceutically acceptable salts and esters thereof, comprising
a) reacting a compound of formula (II),

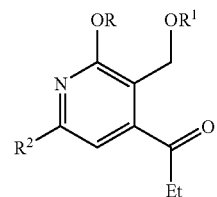
(II)

with a compound of formula (III),

(III)

and b) further reaction in the presence of alkali- or earth alkali metal hydroxides to give the compounds of formula (I), wherein R and $R^1$ are independently alkyl or benzyl, which benzyl is optionally substituted by one, two or three substituents independently selected from
—O-alkyl; alkyl and halogen;

$R^2$ is hydrogen or halogen;

X is $R^3$ and $R^4$ are independently selected from hydrogen, phenyl, alkyl and —C(CH$_3$)$_2$-phenyl;

$R^5$ is phenyl, benzyl or alkyl;

$R^6$ is hydrogen, alkyl or phenyl; and $R^7$ is hydrogen, methyl or phenyl; or alternatively $R^5$ and $R^6$, together with the carbon atoms to which they are attached form an indan-moiety and $R^7$ is hydrogen;

$R^{11}$ and $R^{12}$ are independently alkyl, cycloalkyl, benzyl or phenyl; and $R^{13}$ is phenyl or alkyl.

In another preferred embodiment, the present invention relates to a process for the production of the compounds of formula (I)

and pharmaceutically acceptable salts and esters thereof, comprising a) reacting a compound of formula (II), with a compound of formula (III), and b) further reaction in the presence of alkali- or earth alkali metal hydroxides to give the compounds of formula (I), wherein R is alkyl; and $R^1$ is hydrogen or silyl in formula (I) and silyl in formula (II);

$R^2$ is hydrogen or halogen;

X is $R^5$ is phenyl, benzyl or alkyl;

$R^6$ is hydrogen, alkyl or phenyl; and $R^7$ is hydrogen, methyl or phenyl.

The compounds of formula (I) are useful intermediates for the manufacture of homocamptothecins (hCPT's), some of which are known to show antiproliferative activity.

BACKGROUND OF INVENTION

The alkaloid camptothecin (CPT, 1) shows potent antiproliferative activity and continues to serve as a very attractive lead structure for the development of new anti-cancer drugs (see e.g. in C. J. Thomas, N. J. Rahier, S. M. Hecht, *Bioorg Med Chem.* 2004, 12, 1585-1604). The structure of the pentacyclic skeleton contains a highly electrophilic α-hydroxy-δ-lactone ring (ring "E"), which rapidly hydrolyzes in basic and neutral media yielding the open chain carboxylate form (2, scheme 1), which is almost inactive.

scheme 1

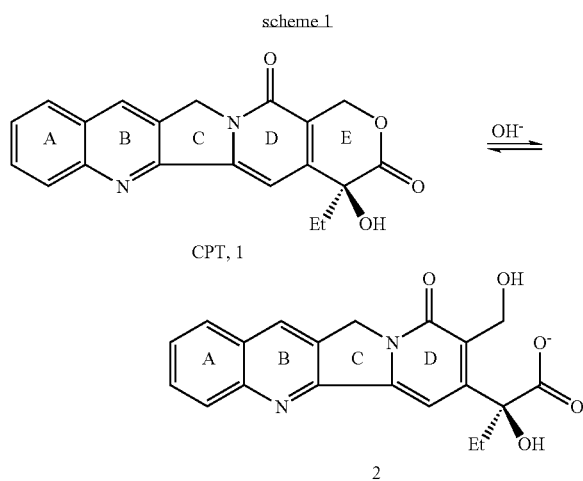

CPT, 1

2

This equilibrium is shifted toward the carboxylate form in human plasma thus explaining the lower efficacy of most CPT analogues in clinical trials.

The development of homocamptothecins (hCPT), which are CPT analogues possessing a seven membered β-hydroxy-ε-lactone ring "E", addressed this issue. Although it was previously generally accepted that an α-hydroxylactone is an indispensable structural feature for anticancer activity, modifications of the CPT-lactone ring which retain the antiproliferative activity and, at the same time, displays enhanced stability against hydrolysis were investigated (Lavergne, Bigg et al., *J. Med. Chem.* 2000, 43, 2285-2289). Therefore hCPT provides an excellent template for the preparation of new, highly cytotoxic compounds, and two promising hCPT derivatives, 3 (Difiomotecan) and 4 (scheme 2), are under investigation for the treatment of cancer.

scheme 2

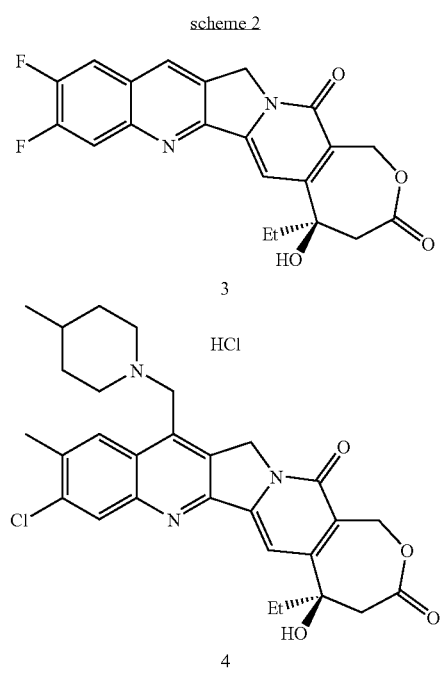

Processes for the manufacture of hCPT's are known in the art (U.S. Pat. No. 6,723,853 B2) principally following the general synthesis route given in scheme 3, wherein "X" and "Y" represent optional substituents (see also Lavergne, Bigg et al., *J. Med. Chem.* 2000, 43, 2285-2289).

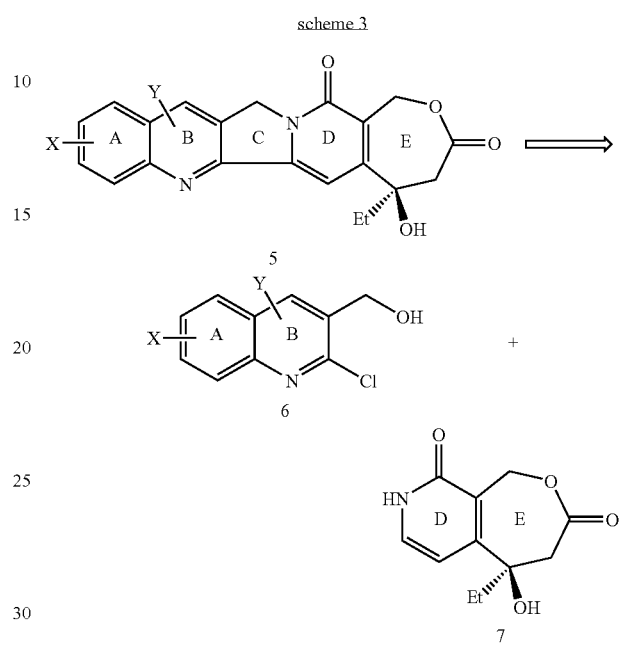

However, when used in large scale manufacture (kg-amounts) these processes suffer from an extremely low yield of typically 0.5% of the bicyclic "DE-fragment", which is essential for the biological activity in the final product. Therefore it remains the need to provide alternative synthesis routes of this fragment.

DETAILED DESCRIPTION OF THE INVENTION

The solution provided by the present invention was found to be an asymmetric acetate aldol addition, leading to improved yields of the compounds of formula (I) which are subsequently transformed into said "DE-fragment", or its derivatives according to the nature of $R^2$ in formula (I). Acetate aldol addition reactions usually suffer from low enantioselectivities. Furthermore, asymmetric acetate aldol additions using ketone substrates are a largely unexplored field. Only few auxiliaries have been reported in literature to provide reasonable stereoselectivities in the addition reaction to acetophenone or similar phenylalkylketones (E. B. Dongala, D. L. Dull, C. Mioskowski, G. Solladié, *Tetrahedron Lett.* 1973, 4983-4986; M. Braun, R. Devant, *Tetrahedron Lett.* 1984, 5031-5034).

It has now surprisingly been found that said bicyclic "DE-fragment" can be obtained in an enantiomerically pure form (er of about 99.95:0.05) and in an overall yield of about 9%, starting from the compounds of formula (IV), scheme 5 and preferably from 2-chloro-4-cyanopyridine when using the process according to the present invention.

As used herein the term "silyl" means a group of the formula $R^{14}R^{15}R^{16}Si-$, wherein $R^{14}$, $R^{15}$ and $R^{16}$ are independently alkyl, cycloalkyl or phenyl. Preferred silyl groups are t-butyldimethylsilyl and t-butyldiphenylsilyl.

As used herein the term "alkyl" means a saturated, linear or branched hydrocarbon containing from 1 to 8, preferably 1 to 6 and more preferably 1 to 4 carbon atoms. Examples of such "alkyl" groups are methyl, ethyl, propyl, isopropyl, 1-butyl, 2-butyl, t-butyl and the like. In this connection the symbols "Me", "Et" and "iPr" as used in the formulae herein mean a methyl-, ethyl- and isopropyl group respectively. In connection with the term "O-alkyl" as used herein the preferred "alkyl" is methyl.

As used herein the term "cycloalkyl" means a saturated mono- or bi-cyclic hydrocarbon consisting of 5 to 10 carbon-atoms. Preferred is a monocyclic hydrocarbon consisting of 5 to 7, more preferably of 6 carbon-atoms. Examples of such cycloalkyl groups are cyclopentyl, cyclohexyl, cycloheptyl, decahydro-naphthyl, octahydro-indyl and the like. According to the present invention, said cycloalkyl groups are unsubstituted or one, two, three or four times, preferably one or two times, substituted by phenyl, benzyl, alkyl, hydroxyl or oxo.

The term "heterocyclyl" as used herein means a mono-, bi- or tricyclic saturated or partially unsaturated or partially aromatic hydrocarbon, wherein one, two, three or four, preferably one or two carbon-atoms are replaced by oxygen, nitrogen or sulfur, preferably oxygen and nitrogen. Examples of such heterocyclic groups are 3,3a,4,8b-tetrahydro-1H-indeno[1,2-c]isoxazol-1-yl; 3,3a,8,8a-tetrahydro-1H-2-thia-3-aza-cyclopenta[a]inden-3-yl; octahydro-indol-1-yl ; octahydro-benzo[c]isothiazol-1-yl ; octahydro-benzo[c]isoxazol-1-yl; 2,3-dihydro-1H-indol-1-yl ; 1,3-dihydro-benzo[c]isothiazol-1-yl ; 1,3-dihydro-benzo[c]isoxazol-1-yl and the like. According to the present invention, said heterocyclyl groups are unsubstituted or one, two, three or four times, preferably one or two times, substituted by phenyl, benzyl, alkyl, hydroxyl or oxo.

In the group "X" of formula (M) as used herein, when "$R^5$ and $R^6$ together with the carbon atoms to which they are attached form an indan-moiety", said group X means

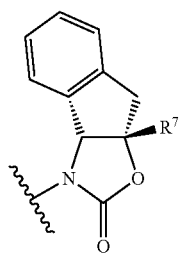

As used herein the term "alkali- or earth-alkali metal amide base" means lithium-, sodium-, potassium- and magnesium amide bases. Examples of such bases are lithium hexamethyldisilazane (LHMDS), lithium diisopropylamide (LDA), 1-lithium-2,2,6,6-tetramethylpiperidine (LTMP), lithium dicyclohexylamide (LiCA), sodium hexamethyldisilazane (NaHMDS), potassium hexamethyldisilazane (KHMDS). Especially preferred is the use of LHMDS.

As used herein the term "optionally substituted" means unsubstituted or one, two or three times substituted.

As used herein the term "ethereal solvents" means solvents from the chemical class of linear or cyclic ethers. Examples of such ethereal solvents are Diethylether ($Et_2O$), 1,2-dimethoxyethane (DME), diisopropylether ($iPr_2O$), tetrahydrofuran (THF) or tert-butyl methyl ether (TBME). Especially preferred is THF.

As used herein the term "mineral acids" means hydrochloric acid (HCl), hydrobromic acid (HBr), trimethylsilyl iodide (TMSI) or boron tribromide ($BBr_3$). Especially preferred is aqueous hydrobromic acid.

As used herein the term "room temperature" (RT) means ambient temperatures in the place where the process according to the present invention is carried out. Said temperatures may vary between 15 and 35° C. Preferably said temperature is between 18 and 28° C., more preferably between 20 and 23° C.

As used herein the term "pharmaceutically acceptable salts and esters" refers to conventional acid-addition salts- or base-addition salts of formula (I), or conventionally esterified compounds of formula (I) and are formed from suitable non-toxic organic or inorganic acids, organic or inorganic bases or from suitable alcohols respectively. Said "pharmaceutically acceptable salts and esters" may for example occur as intermediates during the process of the present invention before the compounds of formula (I) are isolated, or subsequent to their isolation before said compounds of formula (I) are further reacted to give the compounds of formula (A). Sample acid-addition salts include those derived from inorganic acids such as hydrochloric acid, hydrobromic acid, hydroiodic acid, sulfuric acid, sulfurous acid, phosphoric acid and nitric acid, and those derived from organic acids such as p-toluene-sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and quaternary ammonium hydroxides, such as for example, tetramethylammonium hydroxide.

Asymmetric acetate aldol additions using ketone substrates are a largely unexplored field. Very few is known about effective auxiliaries, which are the key factor in order to achieve high selectivities in this type of reaction. It has now been found that good selectivities were obtained with auxiliaries of formula (III), bearing bulky groups in $R^5$ and $R^3$ of the respective formulae as described below. According to the present invention the most promising auxiliaries are chiral oxazolidinones (acylated Evans type auxiliaries). The best selectivities were obtained with such chiral oxazolidinones bearing bulky groups in $R^5$. A substituent $R^6$ cis to $R^5$ was shown to be advantageous both for conversion and selectivity, while a group $R^7$ trans to $R^5$ was shown to have a negative effect. Two auxiliaries are especially preferred according to the present invention: (4R)-4-tert-butyloxazolidin-2-one and (4R,5S)-4,5-diphenyloxazolidin-2-one.

The asymmetric aldol addition according to the present invention is usually carried out in the presence of alkali- or earthalkali metal bases. Preferred bases are lithium-, sodium-, potassium- and magnesium amide bases; lithium-, sodium- and potassium alkyl bases; sodium- and potassium aryl bases; and Grignard reagents. Examples of such bases are lithium hexamethyldisilazane (LHMDS), lithium diisopropylamide (LDA), 1-lithium-2,2,6,6,-tetramethylpiperidine (LTMP), lithium dicyclohexylamide (LiCA), sodium hexamethyldisilazane (NaHMDS), potassium hexamethyldisilazane (KHMDS), butyl lithium (BuLi) also in combination with alkali alkoxides, phenyl lithium (PhLi). Especially preferred is the use of LHMDS.

The process according to the present invention is preferably carried out in ethereal solvents or alkanes. Preferred examples of "ethereal solvents" are Diethylether ($Et_2O$), tetrahydrofuran (THF) or tert-butyl methyl ether (TBME). Preferred examples of alkanes are pentane, hexane or heptane as well as suitable derivatives thereof. The especially preferred solvent is THF.

The process according to the present invention is preferably carried out at temperatures from −120° C. to room temperature (RT). Especially preferred are temperatures from −100 to −60° C.

The subsequent auxiliary cleavage in order to obtain the compounds of formula (I) is carried out using ester- and/or amide cleavage methods well known to the skilled artisan as e.g. described in "T. W. Greene, P. G. M. Wuts, Protective Groups in Organic Synthesis, 3$^{rd}$ edition, Wiley-Interscience 1999". Preferably said auxiliary cleavage is carried out using metal alkoxides, for example alkali and earth alkali metal alkoxides. Especially preferred is the use of lithium hydroxide (LiOH) in combination with hydrogen peroxide (H₂O₂).

Subsequently, the conversion of the compounds of formula (I) into the above-mentioned "DE-fragment", further referred to as the compounds of formula (A), is achieved using conventional Lewis- or Broensted acid promoted ether cleavage methods, which are known to the skilled artisan and described e.g. in "T. W. Greene, P. G. M. Wuts, Protective Groups in Organic Synthesis, 3rd edition, Wiley-Interscience 1999". Preferred is the use of mineral acids like hydrochloric acid (HCl) or hydrobromic acid (HBr), trimethylsilyl iodide (TMSI), boron tribromide (BBr₃). Especially preferred is the method using aqueous hydrobromic acid. This reaction is preferably carried out in ethereal solvents like dimethoxyethane (DME), tetrahydrofuran (THF) or dioxane; or in nitriles like for example acetonitrile (MeCN) and at temperatures from 0 to 120° C., preferably from room temperature (RT) to 60° C.

The final reaction steps in order to obtain the compounds of formula (D) as described herein, especially Diflomotecan, from the compounds of formula (A) is known to the skilled artisan and can generally be performed according to the synthesis route described in scheme 4.

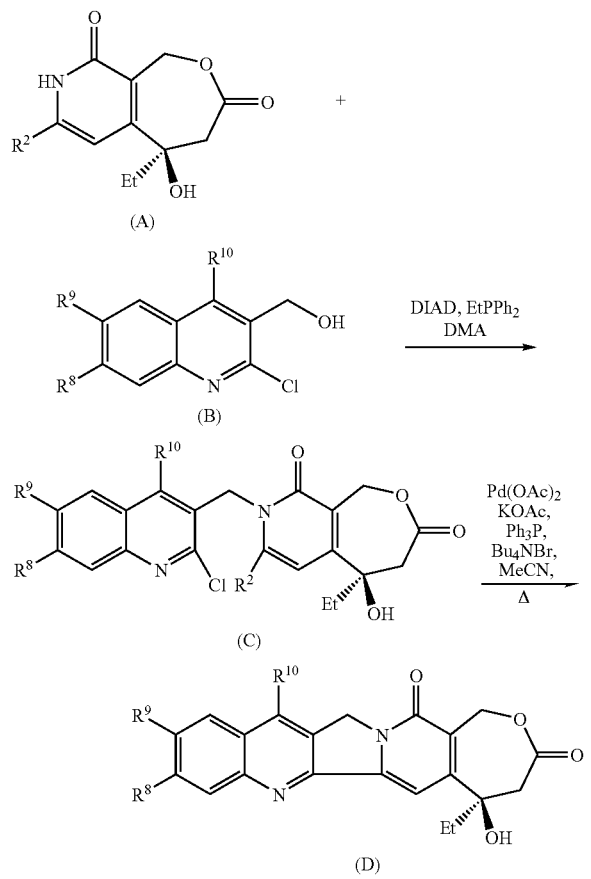

A preferred embodiment of the present invention is the process as described above, wherein X is

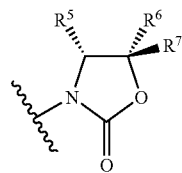

wherein
R⁵ is phenyl, benzyl, isopropyl, tert-butyl or methyl;
R⁶ is hydrogen, methyl or phenyl; and
R⁷ is hydrogen, methyl or phenyl; or alternatively
R⁵ and R⁶ together with the carbon atoms to which they are attached, form an indan-moiety and
R⁷ is hydrogen.

Another preferred embodiment of the present invention is the process as described above, wherein
R¹ is benzyl;
R² is hydrogen; and
X is

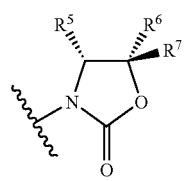

wherein
R⁵ is phenyl, benzyl, isopropyl, tert-butyl or methyl;
R⁶ is hydrogen, methyl or phenyl; and
R⁷ is hydrogen, methyl or phenyl; or alternatively
R⁵ and R⁶ together with the carbon atoms to which they are attached, form an indan-moiety and
R⁷ is hydrogen.

Another preferred embodiment of the present invention is the process as described above, wherein
R⁵ and R⁶ are both phenyl, and
R⁷ is hydrogen.

Another preferred embodiment of the present invention is the process as described above, wherein the compound of formula (I-1)

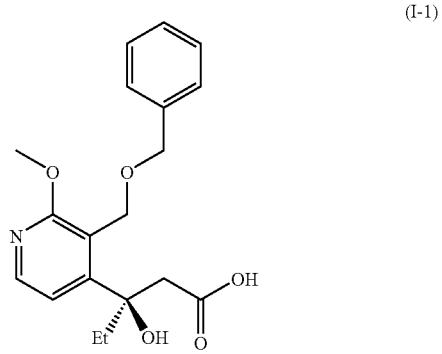

is obtained by
a) reacting the compound of formula (II-1)

(II-1)

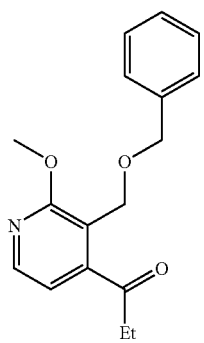

with the compound of formula (III-1)

(III-1)

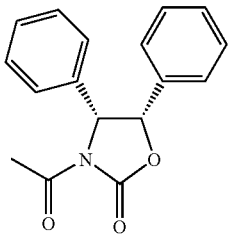

b) further reaction in the presence of lithiumhydroxide in combination with hydrogen peroxide, to give the corresponding compound of formula (I-1).

Another preferred embodiment of the present invention is the process as described above, wherein $R^5$ is phenyl, and $R^6$ and $R^7$ are both hydrogen.

Another preferred embodiment of the present invention is the process as described above, wherein the compound of formula (I-2)

(I-2)

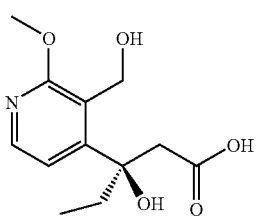

is obtained by a) reacting the compound of formula (II-2)

(II-2)

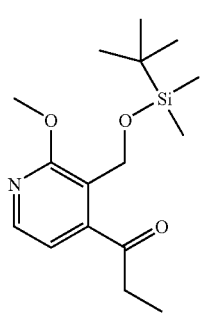

with the compound of formula (III-2)

(III-2)

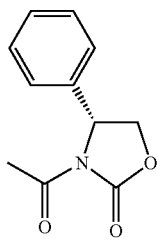

b) further reaction in the presence of lithiumhydroxide in combination with hydrogen peroxide, to give the corresponding compound of formula (I-2).

Yet another embodiment of the present invention is the process as described herein before, whereby the process step a) is carried out in the presence of an alkali- or earth-alkali metal amide base.

Yet another embodiment of the present invention is the process as described herein before, whereby the process step a) is carried out in the presence of lithium hexamethyldisilazane (LHMDS).

Yet another embodiment of the present invention is the process as described herein before, whereby the process step a) is carried out in the presence of diethylether ($Et_2O$), tetrahydrofuran (THF), tert-butyl methyl ether (TBME), pentane, hexane or heptane.

Yet another embodiment of the present invention is the process as described above, whereby the process step a) is carried out in the presence of tetrahydrofuran.

Yet another embodiment of the present invention is the process as described herein before, whereby the process step a) is carried out at temperatures in the range between 25° C. and −120° C.

Yet another embodiment of the present invention is the process as described above, whereby the process step a) is carried out at temperatures in the range between −60° C. and −100° C.

Yet another embodiment of the present invention is the process as described above, whereby the process step a) is carried out at temperatures between −90° C. and −100° C.

Yet another embodiment of the present invention is the process as described herein before, whereby the process step b) is carried out in the presence of an alkali- or earth alkali metal hydroxide, alone or in combination with hydrogen peroxide.

Yet another embodiment of the present invention is the process as described herein before, whereby the process step b) is carried out in the presence of lithium hydroxide in combination with hydrogen peroxide.

Yet another embodiment of the present invention is the process as described herein before, wherein X is

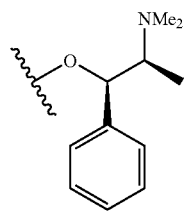

The compounds of formula (I), obtainable by the new process according to the present invention, are valuable intermediates for the manufacture of the homocamptothecins of formula (D). Some homocamptothecins, for example Diflomotecan, show antiproliferative activity and are therefore useful in the treatment and/or prevention of diseases related to abnormal cell proliferative activities, especially cancer.

Therefore, another embodiment of the present invention is the process as described above, wherein the compound of formula (I) is subsequently converted into a compound of formula (A)

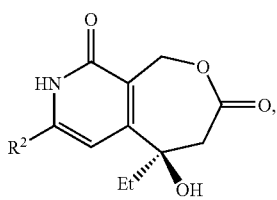

in the presence of a mineral acid and an ethereal solvent at temperatures between room temperature (RT) and 60° C.

Still another embodiment of the present invention is the process as described above, wherein said compound of formula (A) is further reacted with a compound of formula (B)

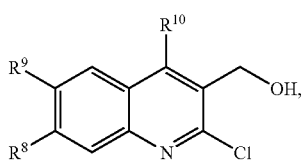

in the presence of diisopropyl azodicarboxylate (DIAD), ethyidiphenylphosphine (EtPPh$_2$) and dimethylacetamide (DMA), to give a compound of formula (C)

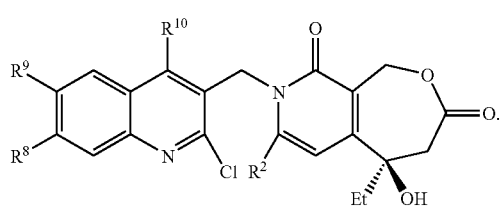

Still another embodiment of the present invention is the process as described above, wherein said compound of formula (C) is further reacted in the presence of palladium (II) acetate (Pd(OAc)$_2$), potassium acetate (KOAc), triphenylphosphine (Ph$_3$P), tetrabutyl ammonium bromide (Bu$_4$NBr) and acetonitrile (MeCN) to give the corresponding compound of formula (D)

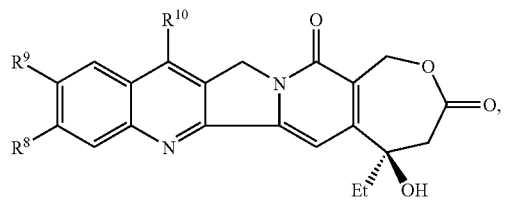

wherein

R$^2$ has the significance given herein before;

R$^8$ and R$^9$ are independently alkyl or halogen; and

R$^{10}$ is 4-methyl-piperidin-1-ylmethyl or hydrogen.

Yet another embodiment of the present invention is the process as described above, wherein said compound of formula (I) is transformed into a compound of formula (D)

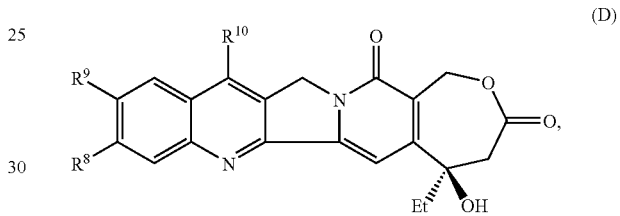

by:

a) converting said compound of formula (I) into a compound of formula (A)

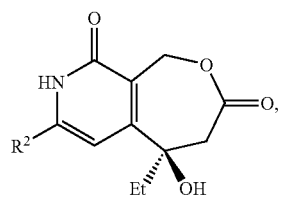

in the presence of a mineral acid and an ethereal solvent at temperatures between room temperature (RT) and 60° C.; and b) further reacting said compound of formula (A) with a compound of formula (B)

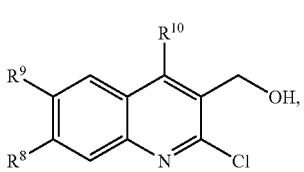

in the presence of diisopropyl azodicarboxylate (DIAD), ethyldiphenylphosphine (EtPPh$_2$) and dimethylacetamide (DMA), to give a compound of formula (C)

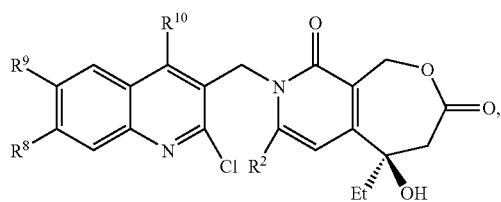

and c) said compound of formula (C) is further reacted in the presence of palladium (II) acetate (Pd(OAc)$_2$), potassium acetate (KOAc), triphenylphosphine (Ph$_3$P), tetrabutyl ammonium bromide (Bu$_4$NBr) and acetonitrile (MeCN) to give the corresponding compound of formula (D)

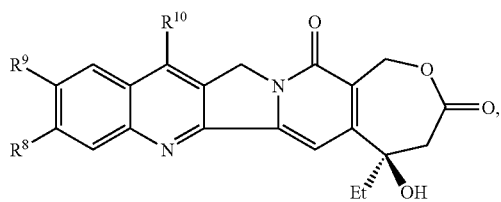

wherein $R^2$ has the significance given herein before;
$R^8$ and $R^9$ are independently alkyl or halogen; and
$R^{10}$ is 4-methyl-piperidin-1-ylmethyl or hydrogen.

Yet another embodiment of the present invention is the process as described above, wherein $R^2$ and $R^{10}$ are both hydrogen, and $R^8$ and $R^9$ are both fluorine.

Still another embodiment of the present invention is the process as described above, wherein $R^2$ is hydrogen, $R^{10}$ is 4-methyl-piperidin-1-ylmethyl, $R^8$ is chlorine and $R^9$ is methyl.

Still another embodiment of the present invention is the process as described above, wherein the process step a) is carried out in the presence of hydrobromic acid (HBr) and dimethoxyethane (DME) at temperatures between 45 and 55° C.

Still another embodiment of the present invention are the compounds of the general formula (I)

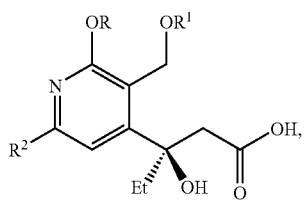

wherein

R and $R^1$ are independently alkyl, or benzyl, which benzyl is optionally substituted by —O-alkyl; alkyl and halogen; and
if R is alkyl $R^1$ can also be hydrogen;
$R^2$ is hydrogen or halogen.

Still another embodiment of the present invention are the compounds of the general formula (I)

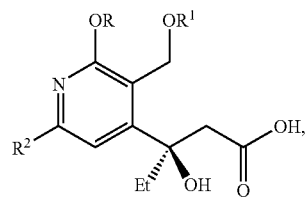

wherein

R and $R^1$ are independently allyl or benzyl, which benzyl is optionally substituted by —O-alkyl; alkyl and halogen; and
$R^2$ is hydrogen or halogen.

Still another embodiment of the present invention are the compounds as defined above, wherein
$R^2$ is halogen.

Still another embodiment of the present invention are the compounds as defined above, wherein
R and $R^1$ are independently alkyl or benzyl, which benzyl is substituted by —O-alkyl; alkyl and halogen.

Still another embodiment of the present invention is the compound of formula (I)
(R)-3-(3-benzyloxymethyl-2-methoxy-pyridin-4-yl)-3-hydroxy-pentanoic acid.

Still another embodiment of the present invention is the compound of formula (I)
(R)-3-Hydroxy-3-(3-hydroxymethyl-2-methoxy-pyridin-4-yl)-pentanoic acid.

Still another embodiment of the present invention is the use of the compounds as defined above in the process as described herein before.

Still another embodiment of the present invention is the use of the compound

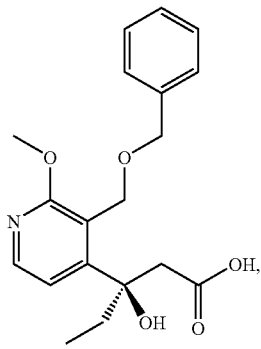

for the manufacture of the compounds represented by the formulae

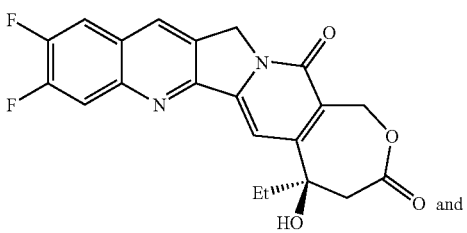

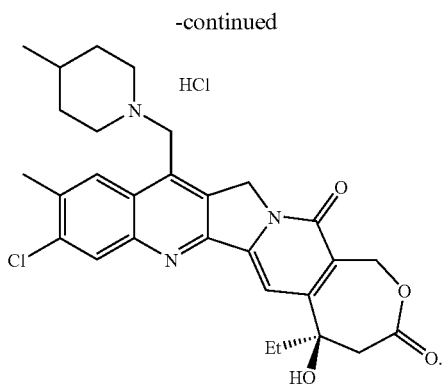

Still another embodiment of the present invention is the use of the compound

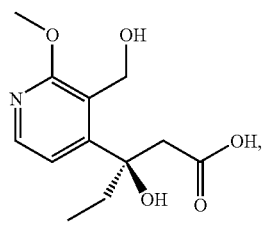

for the manufacture of the compounds represented by the formulae

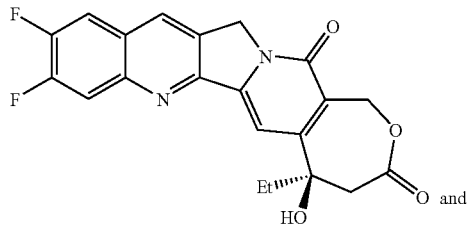

and

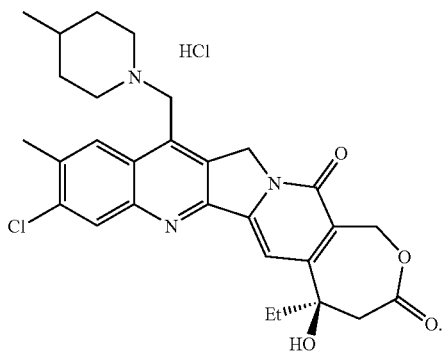

Still another embodiment of the present invention is the use of the process as described above for the preparation of the compounds of formula (I).

Still another embodiment of the present invention is the use of the process as described above in the manufacture of the compound with the formula

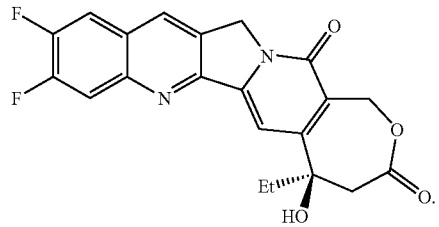

The compounds of formula (II), wherein R and $R^1$ are independently alkyl or optionally substituted benzyl and $R^2$ has the meaning given herein before, can be obtained by any process known to be applicable by the skilled artisan. According to the present invention the synthesis route as described in scheme 5 is especially preferred. Although being based on a known synthesis, the steps leading to the compounds of formula (II) were improved according to the present invention. This is because the purity of the ketones of formula (II) when obtained according to the known method, is not sufficient for the development of an asymmetric aldol addition reaction as described by the present invention. Especially the reaction conditions for steps 4 to 7 have been modified, resulting in higher yield and better quality of the ketones of formula (II), scheme 5.

Consequently the particular reaction conditions as described below for the reaction steps 1 to 7 of scheme 5 and in the accompanying non-limiting examples are a further embodiment of the present invention.

scheme 5

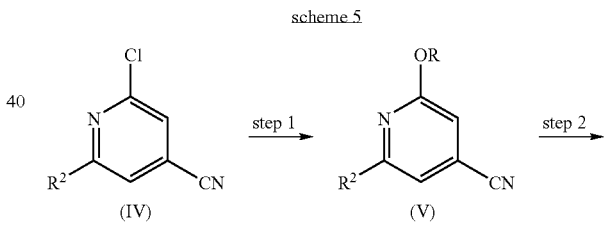

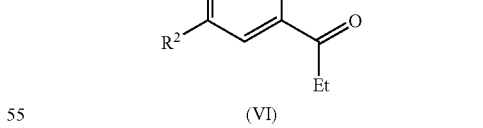

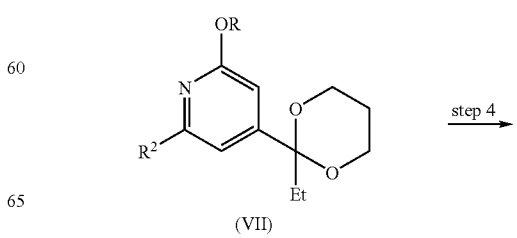

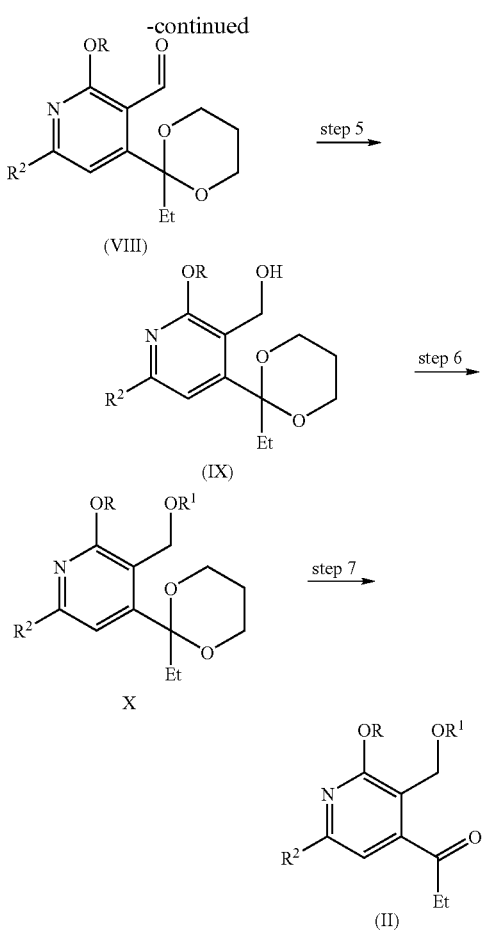

Steps 1 and 2:

These reactions are an alkanolysis of the starting material 2-chloro-4-cyano-pyridine, followed by a Grignard addition (step 2). Both reactions are well known to the skilled artisan. However, according to the present invention an amount between 0.5 to 3.0 equivalents (eq) sodium methoxide (NaOMe), preferably 1.0 to 1.5 eq, most preferably 1.0 to 1.2 eq, was used in step 1. The product is purified by soxhlet extraction. The following Grignard addition is preferably carried out in tert-butyl methyl ether (TBME) as solvent.

Step 3:

During the acetal formation with propanediol, it was realized that the conversion strongly depends on the amount of acid catalyst used. In several cases, no conversion was realized even after 24 h with 2 mol % of para-toluenesulphonic acid (PTSA); however, with additional PTSA or sulfuric acid ($H_2SO_4$), the reaction was complete after 24 h. After these steps, the acetals of formula (VII) can be isolated in about 40% yield and with an HPLC purity >95% area after high vacuum distillation. These improvements are essential for the subsequent sensitive metalation of the pyridine 3-position.

Step 4:

In order to carry out the metalation of the pyridine 3-position we found that the concentration of an n-Butyllithium (n-BuLi) solution in hexane is a key parameter, which can be optimized instead of using the common 1.6 M n-BuLi in hexane solution. When using 1.7 to 4 M, preferably 2.0 to 3.0 M solutions of n-BuLi in hexane the amount of hexane, which is crucial for the solubility of mesithyl-lithium (MesLi), can be reduced. The lithiated species was then trapped by dimethyl formamide (DMF) resulting in the aldehydes of formula (VIII), scheme 5. The advantages of this procedure are high conversions as well as the ease of product purification by silica gel filtration to remove mesityl side products and unreacted starting material as well as other side products. The most prominent side product was identified by LC-MS and NMR as mesityl addition product to the pyridine-6-position.

Step 5:

A reduction step with sodium borohydride ($NaBH_4$) is now required, thus providing the compounds of formula (IX), scheme 5 in high yield and purity after trituration with heptane.

Step 6:

In the subsequent benzylation step, it was desirable to replace sodium hydride (NaH), as used in the known procedure, by an alternative base. In addition to the safety issue, which is raised by NaH, we encountered formation of considerable amounts of high boiling dibenzyl ether as side product depending on the NaH quality. According to the present invention non-nucleophilic lithium bases are preferred. Especially preferred is lithium hexamethyl-disilazane (LHMDS), which is available as THF solution for clean preformation of the corresponding lithium alkoxide. By addition of 10 mol % of dry tetrabutylammonium iodide (TBAI), the alkylation proceeds without major decomposition at 65° C., furnishing the compounds of formula (X), scheme 5 in high purity. In order to remove excess of benzyl bromide, pyrrolidine was added after almost complete conversion and the resulting tertiary benzylamine was removed by extraction with aqueous hydrogen chloride (HCl). Surprisingly, the addition of pyrrolidine at the end of the reaction also resulted in an acceleration of benzylation of unreacted starting material (IX, scheme 5).

Step 7:

According to the present invention, the subsequent acetal cleavage is carried out utilizing a catalytic amount of para-toluenesulfonic acid (PTSA, 0.2 eq) in a mixture of Ethanol/water (4:1). Under these conditions, the crude ketones of formula (II) are isolated in high purity.

The compounds of formula (II), wherein R is alkyl, $R^1$ is silyl and $R^2$ has the meaning given herein before, can be obtained by any process known to be applicable by the skilled artisan. According to the present invention the synthesis route as described in scheme 6 is especially preferred in order to avoid the sophisticated use of mesityl-lithium (MesLi) and the related problems, such as the elaborate conditions for the in situ generation of MesLi and the formation of high boiling mesityl side products only removable by silica gel filtration.

scheme 6

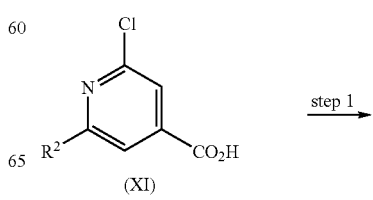

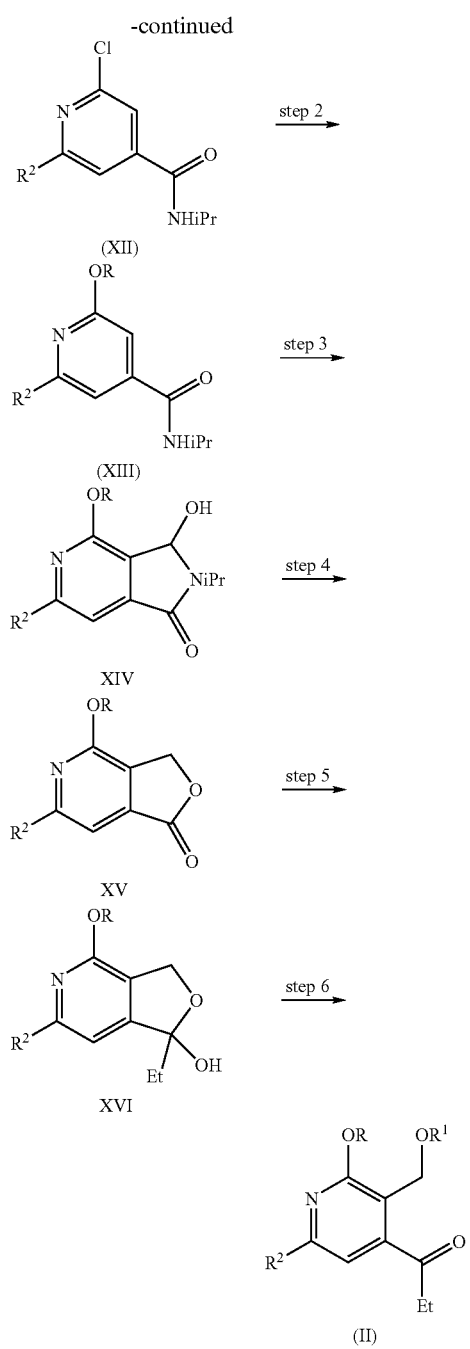

low in TBF (3-Li/5-Li=ca. 3:1), metalation of the 3-position is significantly favored in TBME. The lithiated species is trapped by DMF yielding the N,O-hemiacetals of formula (XIV).

Step 4:

The crude product of step 3, which still contains large amounts of DMF, is reduced by $NaBH_4$ in isopropanol/water to the corresponding hydroxyamide, which is then cyclized in the same pot by addition of aqueous HCl furnishing the lactones of formula (XV) which are purified by trituration. According to the present invention, the choice of an isopropanol/water mixture for this reduction step is especially preferred in order to reduce the amount of $NaBH_4$.

Step 5:

According to the present invention, the addition of ethyl to the lactones of formula (XV) to provide the lactols of formula (XVI) is preferably carried out using ethyllithium (EtLi). Especially preferred is the use of a combination of triethylaluminum ($AlEt_3$) and ethyllithium. Equimolar amounts of $AlEt_3$ and EtLi are pre-coordinated at 0° C. The solution of the starting material (XV) is then rapidly added at −40° C. In order to reach a high conversion, a second equivalent of EtLi is required, which is slowly added at −40° C., before the reaction mixture is allowed to slowly warm up to −15° C.

Step 6:

In order to obtain the ketone substrates of formula (II) for the asymmetric aldol addition reaction according to the present invention, the compound of formula (XVI) has to be opened by an appropriate electrophile. As a further feature of the present invention, silyl chlorides and especially t-butyldimethylsilyl-chloride (TBSCl) and t-butyldiphenylsilyl-chloride (TBDPSCl) are preferred. The workup of the TBS and TBDPS ether formation benefits from the heptane solubility of the lipophilic silyl ethers. As a result, the polar components DMF and imidazole were completely removed by aqueous workup and the crude ketones of formula (II) can be obtained in high purity.

The following examples and references are provided to aid the understanding of the present invention, the true scope of which is set forth in the appended claims. It is understood that modifications can be made in the procedures set forth without departing from the spirit of the invention.

In the following Examples, if not explicitly otherwise stated, analytical High Performance Liquid Chromatography (HPLC) was performed according to the following protocol:

Steps 1 and 2:

2-Methoxy-4-isopropylamides of formula (XIII) are prepared over two steps starting from 2-chloroisonicotinic acids of the formula (XI), which are first activated by formation of the corresponding acid chloride and then reacted in the same pot with isopropylamine. The 2-chloro substituent is subsequently substituted by a methoxy group using NaOMe.

Step 3:

Metalation of the 3-position of the compounds of formula (XIII) according to the present invention is preferably carried out with n-BuLi in the presence of TMEDA or lithium chloride (LiCl). Butyl addition to the pyridine-6-position was never observed for this substrate. While the regioselectivity is

| | |
|---|---|
| Method | SEVLM |
| | Sample preparation: 5 μL of the reaction mixture were added to 0.2 mL acetonitrile/water (9:1). |
| Equipment | HP 1050 Series HPLC system |
| Column | Chromolith, Performance 100x4.6 |
| Temperature | 40° C. |
| Mobile phase | gradient (3 components A-C) |
| | A: water |
| | B: 800 ml water, 200 ml acetonitrile, 1 g TBAHS |
| | C: acetonitrile |
| Flow | 2.0 ml/min |
| Injection volume | 1 μl |
| Detection | UV 210 nm |

EXAMPLE 1

Synthesis of 2-methoxy-isonicotinonitrile

A stirred suspension of 17.86 g NaOMe (330.7 mmol, 1.22 eq) in 95 mL acetonitrile was cooled to 0° C. and a solution of 37.56 g 2-chloro-4-cyano pyridine (8, 271.1 mmol) in 225 mL acetonitrile was added over 45 min. Stirring was continued at room temperature for 23 h until less than 4% (area) starting material were detected by HPLC. 11.1 g potassium dihydrogen phosphate (81.56 mmol, 0.30 eq) were added at 0° C. and stirring was continued for 3 h at room temperature. The reaction mixture was then evaporated to dryness in a rotary evaporator (40° C./10 mbar) yielding the crude product (64.94 g, 179% by weight) as a brown solid. 64.94 g crude product were extracted with 900 mL toluene for 18 h at reflux temperature using a soxhlet extraction apparatus yielding the title product (25.65 g, 71% by weight) as an orange solid.

Mp: 98° C.;
$^1$H NMR (300 MHz, CDCl$_3$): δ 8.31 (d, 1H, J=5.1 Hz), 7.07 (dd, 1H, J=5.1 Hz, J=1.2 Hz), 6.99 (br. s, 1H), 3.97 (s, 3H) ppm.

EXAMPLE 2

Synthesis of 1-(2-methoxy-pyridin-4-yl)-propan-1-one

A stirred suspension of 25.44 g of 2-methoxy-isonicotinonitrile as obtained in Example 1 (189.7 mmol) in 380 mL TBME was cooled to 0° C. and 114 mL ethyl magnesium chloride in THF (2.0 M, 228.0 mmol, 1.20 eq) were added within 45 min. Stirring was continued at 0° C. After 3 h 40 min, additional 5 mL ethyl magnesium chloride in THF (2.0 M, 10.0 mmol, 0.05 eq) were added at 0° C. The reaction was monitored by HPLC. After 4.5 h (<3% area 2-methoxy-isonicotinonitrile), the reaction was quenched at 0° C. by addition of 300 mL water. The resulting suspension was stirred for 16 h at room temperature and was then diluted with 200 mL toluene. The aqueous phase was extracted with 400 mL toluene and the combined organic phases were washed with 500 mL saturated aqueous NH$_4$Cl and 500 mL brine, dried over 50 g Na$_2$SO$_4$ (30 min) and filtered. The filter cake was washed with 100 mL toluene. After evaporation of solvent in a rotary evaporator (40° C./10 mbar), the title compound (28.64 g, 91% by weight) was obtained as an orange solid.

Mp: 38° C.;
$^1$H NMR (300 MHz, CDCl$_3$): δ 8.30 (d, 1H, J=5.3 Hz), 7.30 (dd, 1H, J=5.3 Hz, J=1.8 (br. s, 1H), 3.98 (s, 3H), 2.96 (q, 2H, J=7.2 Hz), 1.22 (t, 3H, J=7.2 Hz) ppm

EXAMPLE 3

Synthesis of 4-(2-ethyl-[1,3]dioxan-2-yl)-2-methoxy-pyridine

To a stirred solution of 38.23 g of 1-(2-methoxy-pyridin-4-yl)-propan-1-one (231.4 mmol) as obtainable from Example 2 in 575 mL toluene were added 100 mL 1,3-propandiol (1.39 mol, 6.0 eq), 473 μL sulfuric acid (4.63 mmol, 0.02 eq) and 889 mg para-toluene sulfonic acid monohydrate (4.63 mmol, 0.02 eq). The reaction mixture was heated for 72 h (NMR control: <2% starting material 1-(2-methoxy-pyridin-4-yl)-propan-1-one) to reflux using a Dean-Stark trap (oil bath temperature 160° C.). After cooling down to room temperature, 500 mL saturated aqueous NaHCO$_3$ were added and the phases were separated. The organic phase was washed twice with 250 mL, in total with 500 mL brine and was then dried over 50 g Na$_2$SO$_4$ (30 min) and filtered. The filter cake was washed with 100 mL toluene. After evaporation of solvent in a rotary evaporator (50° C./10 mbar), the crude product (40.31 g, 78% by weight) was obtained as a brown oil (HPLC purity 93.9% area). Purification was achieved using a high vacuum distillation (bp 95° C. at 0.056 mbar, oil bath temperature 125° C., 40 cm Vigreux column) furnishing the title compound (31.80 g, 142.4 mmol, 62% by weight) as colourless liquid.

Bp: 95° C. (0.056 mbar);
$^1$H NMR (300 MHz, CDCl$_3$): δ 8.19 (dd, 1H, J=5.2 Hz, J=0.8 Hz), 6.91 (dd, 1H, J=5.3 Hz, J=1.5 Hz), 6.78 (dd, 1H, J=1.4 Hz, J=0.8 Hz), 3.96 (s, 3H), 3.89 (m, 2H 3.75 (m, 2H), 2.09 (m, 1H), 1.72 (q, 2H, J=7.5 Hz), 1.26 (m, 1H), 0.81 (t, 3H, J=7.5 Hz ppm

EXAMPLE 4

Synthesis of 4-(2-ethyl-[1,3]dioxan-2-yl)-2-methoxy-pyridine-3-carbaldehyde

A stirred solution of 6.87 mL 2-bromomesitylene (44.78 mmol, 2.0 eq) in 44 mL THF was cooled to −45° C. 35.8 mL n-butyllithium in hexane (2.5 M, 89.56 mmol, 4.0 eq) were added within 20 min. The resulting white suspension was then allowed to warm to 0° C. within 2.5 h. At −10° C. the reaction mixture became a clear solution. Stirring was continued for an additional hour at 0° C. The solution was cooled to −10° C. and a solution of 5.00 g 4-(2-ethyl-[1,3]dioxan-2-yl)-2-methoxy-pyridine (22.39 mmol), as obtainable from Example 3, in 15 mL THF was added over 15 min under vigorous stirring. The resulting brown suspension was allowed to warm to 10° C. within 2.5 h. The cooling bath was then removed and stirring was continued at room temperature for an additional hour. The clear brown solution was then cooled to −23° C. and 5.19 mL DMF (67.17 mmol, 3.0 eq) were added. The mixture was allowed to slowly warm up to room temperature overnight. The reaction was quenched by addition of 100 mL saturated aqueous NH$_4$Cl. After 15 min, 50 mL water were added. The mixture was extracted three times with 150 mL, in total with 450 mL TBME. The combined organic phases were washed two times with 300 mL, in total 600 mL brine, dried over 20 g Na$_2$SO$_4$ (30 min) and filtered. The filter cake was washed with 40 mL TBME. After evaporation of solvent in a rotary evaporator (40° C./10 mbar), the crude product (12.048 g, 214% by weight) was obtained as a brown oil which was then purified by silica gel filtration (97 g silica gel) using a gradient elution with 2.0 L heptane/ethyl acetate (30:1) and 1.4 L heptane/ethyl acetate (5:1). Evaporation to dryness of the second fraction in a rotary evaporator (40° C./10 mbar) yielded the title compound (3.832 g, 15.2 mmol, 68% by weight).

$^1$H NMR (300 MHz, CDCl$_3$): δ 10.33 (s, 1H), 8.25 (d, 1H, J=5.5 Hz), 6.96 (d, 1H, J=5.3 Hz), 3.98 (s, 3H), 3.83 (m, 2H), 3.61 (m, 2H), 2.09 (m, 1H), 1.86 (q, 2H, J=7.5 Hz), 1.29 (m, 1H), 0.92 (t, 3H, J=7.5 Hz) ppm;

EXAMPLE 5

Synthesis of [4-(2-ethyl-[1,3]dioxan-2-yl)-2-methoxy-pyridin-3-yl]-methanol

To stirred solution of 3.178 g of 4-(2-ethyl-[1,3]dioxan-2-yl)-2-methoxy-pyridine-3-carbaldehyde as obtained from Example 4 (12.65 mmol) in 95 mL isopropanol and 15.8 mL water were added at 0° C. 134.6 mg sodium borohydride (3.416 mmol, 0.27 eq). The reaction was monitored by HPLC, and after 30 min (<0.2% area starting material as obtained from Example 4), the reduction was quenched by addition of 11 mL acetone and stirring was continued for 30 min at room temperature. 190 mL saturated aqueous NH$_4$Cl were added and the mixture was extracted three times with 180 mL, in total with 540 mL dichloromethane. The combined organic phases were dried over 20 g Na$_2$SO$_4$ (30 min) and filtered. The solid was washed with 40 mL dichloromethane. After evaporation of solvent in a rotary evaporator (40° C./10 mbar), the crude product (3.184 g, 99% by weight) was obtained as a yellow oil. Purification was achieved by trituration with 16 mL heptane for 24 h at room temperature and subsequent standing for 4 days at −20° C. After cold filtration and removal of residual solvent in a rotary evaporator (40° C./10 mbar), the title compound (2.827 g, 11.2 mmol, 88% by weight) was obtained as white crystals.

Mp: 79° C.;

$^1$H NMR (300 MHz, CDCl$_3$): δ 8.11 (d, 1H, J=5.3 Hz), 7.01 (d, 1H, J=5.3 Hz), 4.93 (d, 2H, J=6.6 Hz), 4.04 (s, 3H), 3.93 (m, 2H), 3.77 (m, 2H), 2.83 (t, 1H, J=7.2 Hz), 2.10 (m, 1H), 1.81 (q, 2H, J=7.5 Hz), 1.30 (m, 1H), 0.85 (t, 3H, J=7.4 Hz) ppm

EXAMPLE 6

Synthesis of 3-benzyloxymethyl-4-(2-ethyl-[1,3] dioxan-2-yl)-2-methoxy-pyridine

To a stirred solution of 3.828 g [4-(2-ethyl-[1,3]dioxan-2-yl)-2-methoxy-pyridin-3-yl]-methanol as obtained from Example 5 (15.11 mmol) in 21 mL THF were added within 10 min and at −78° C. 16.6 mL lithium bis(trimethylsilyl)amide in THF (1.0 M, 16.62 mmol, 1.1 eq). After additional 10 min at −78° C., stirring was continued for 10 min at 0° C. and for 15 min at room temperature. 2.56 mL benzylbromide (21.15 mmol, 1.4 eq) and 570 mg tetrabutylammonium iodide (1.51 mmol, 0.1 eq) were subsequently added and the mixture was heated to 65° C. The reaction was monitored by HPLC. After 16 h at 65° C. (<2% area starting material as obtained from Example 5), 250 μL pyrrolidine (3.02 mmol, 0.2 eq) were added at room temperature. After 1 h at room temperature (<0.2% area starting material as obtained from Example 5), additional 625 μL pyrrolidine (3.02 mmol, 0.2 eq) were added. After 2.5 h (<0.1% area benzylbromide), the mixture was poured into 600 mL heptane and the organic phase was washed twice with 400 mL, in total with 800 mL aqueous HCl (0.5 M) and subsequently with 500 mL water. The organic phase was dried over 20 g Na$_2$SO$_4$ (30 min) and filtered. The solid was washed with 40 mL heptane. After evaporation of solvent in a rotary evaporator (40° C./10 mbar), the title compound (4.985 g, 96% by weight) was obtained as a yellow oil.

$^1$H NMR (300 MHz, CDCl$_3$): δ 8.12 (d, 1H, J=5.5 Hz), 7.25-7.41 (m, 5H), 6.98 (d, 1H J=5.4 Hz), 4.73 (s, 2H), 4.63 (s, 2H), 3.98 (s, 3H), 3.85 (m, 4H), 2.09 (m, 1H), 1.80 (q, 2H, J=7.5 Hz), 1.24 (dm, 1H, J=13.0 Hz), 0.84 (t, 3H, J=7.4 Hz) ppm

EXAMPLE 7

Synthesis of 1-(3-benzyloxymethyl-2-methoxy-pyridin-4-yl)-propan-1-one

To stirred solution of 4.120 g 3-benzyloxymethyl-4-(2-ethyl-[1,3]dioxan-2-yl)-2-methoxy-pyridine as obtained from Example 6 (12.00 mmol) in 96 mL ethanol and 24 mL water were added at room temperature 461 mg para-toluenesulfonic acid monohydrate (2.40 mmol, 0.2 eq). The mixture was subsequently heated to 80° C. and the reaction was monitored by HPLC and after 6.25 h at 80° C. (<0.2% area starting material as obtained from Example 6), the solution was cooled down to room temperature and poured into 600 mL heptane. The organic phase was washed with 600 mL water, subsequently with 600 mL aqueous NaHCO$_3$ solution (0.1 M) and again with 600 mL water. The organic phase was dried over 20 g Na$_2$SO$_4$ (30 min) and filtered. The solid was washed with 40 mL heptane. After evaporation of solvent in a rotary evaporator (40° C./10 mbar), the title compound (3.302 g, 96% by weight) was obtained as a light yellow oil.

$^1$H NMR (300 MHz, CDCl$_3$): δ 8.14 (d, 1H, J=5.1 Hz), 7.29-7.37 (m, 5H), 6.75 (d, 1H J=5.3 Hz), 4.62 (s, 2H), 4.50 (s, 2H), 3.95 (s, 3H), 2.74 (q, 2H, J=7.2 Hz), 1.06 (t, 3H, J=7.2 Hz) ppm

EXAMPLE 8

Synthesis of (4R,5S)-3-acetyl-4,5-diphenyl-oxazolidin-2-one

To a stirred suspension of 5.100 g (4R,5S)-(+)-cis-4,5-diphenyl-2-oxazolidinone (20.89 mmol) in 102 mL THF, were added 13.65 mL n-butyllithium in hexane (1.5 M, 20.47 mmol, 0.98 eq) at −78° C. during 6 min. The resulting dark red solution was stirred for additional 68 min at −78° C. During this period, the solution became colorless. Stirring was continued for 15 min at −25° C., before it was cooled again to −78° C. A solution of 1.536 mL acetyl chloride (21.31 mmol, 1.02 eq) in 15.3 mL THF was then added within 5 min. After 52 min, the mixture was poured on 510 mL water and the product was extracted three times with 305 mL, in total 915 mL dichloromethane. The combined organic phases were washed with 715 mL aqueous NaHCO$_3$ and with 715 mL brine. The solution was dried over 25 g sodium sulfate (30 min) and filtered. The filter cake was washed with 50 mL dichloromethane. After removal of solvent in a rotary evaporator (40° C., 30 mbar), the crude product (5.899 g, 100% by weight) was obtained as a white solid. Purification was accomplished by recrystallization from 13 mL toluene. The heterogeneous mixture was heated to reflux until a clear solution was obtained, which was then allowed to slowly cool down to room temperature. After two days, the title compound was collected by filtration as white crystals (5.157 g, 18.332 mmol, 88% by weight).

Mp: 142° C.;

$^1$H NMR (300 MHz, CDCl$_3$): δ 7.11 (m, 6H), 6.97 (m, 2H), 6.86 (m, 2H), 5.91 (d, 1H, J=7.5 Hz), 5.67 (d, 1H, J=7.5 Hz), 2.62 (s, 3H) ppm

EXAMPLE 9

Synthesis of (4R,5S)-3-[(R)-3-(3-benzyloxymethyl-2-methoxy-pyridin-4-yl)-3-hydroxy-pentanoyl]-4,5-diphenyl-oxazolidin-2-one A 10 ml round bottomed flask was charged with 389.4 μL lithium bis(trimethylsilyl)amide solution (1.0 M in THF, 0.385 mmol, 1.1 eq) and the solution was cooled to −78° C. 108.4 mg (4R,5S)-3-acetyl-4,5-diphenyl-oxazolidin-2-one (0.385 mmol, 1.1 eq), as obtainable from Example 8, in 650 μL THF were slowly added (addition time: 5 min). During the addition, the color changed from colorless to bright yellow. After 2 h at −78° C., the solution was cooled to −95° C. and 100.0 mg 1-(3-benzyloxymethyl-2-methoxy-pyridin-4-yl)- propan-1-one (0.350 mmol), as obtainable from Example 7, dissolved in 400 µL THF were slowly added (addition time: 5 min). The solution was kept for additional 30 min at −95° C. and then for 45 min at −78° C. Subsequently, the reaction was quenched by addition of 5 mL aqueous 0.5 M HCl. The mixture was extracted three times with 10 mL, in total 30 mL dichloromethane and the combined extracts were dried over 1 g sodium sulfate (30 min) and filtered. The filter cake was washed with 2 mL dichloromethane. After removal of solvent in a rotary evaporator (40° C., 5 mbar), the title compound was obtained as a colorless oil (206.7 mg, 104% by weight, dr=92:8 ($^1$H-NMR).

Mp: 61° C.;
$[\alpha]_D^{20}$ (c=0.7417 g/dL, CHCl$_3$)=−23.9;
$^1$H NMR (300 MHz, CDCl$_3$): δ 7.99 (d, 1H, J=5.6 Hz), 6.83-7.33 (m, 15H), 6.57 (d, 1H, J=5.6 Hz), 5.79 (d, 1H, J=7.7 Hz), 5.51 (d, 1H, J=7.7 Hz), 5.31 (s, 1H), 4.89 (d, 1H, J=10.5 Hz), 4.81 (d, 1H, J=10.6 Hz), 4.42 (d, 1H, J=11.6 Hz), 4.35 (d, 1H, J=16.8 Hz), 4.33 (d, 1H, J=11.8 Hz), 3.90 (s, 3H), 3.22 (d, 1H, J=16.8 Hz), 1.92 (q, 2H J=7.1 Hz), 0.80 (t, 3H, J=7.4 Hz) ppm
$^{13}$C NMR (100 MHz, CDCl$_3$): δ 171.1, 163.8, 156.2, 153.6, 145.9, 138.5, 133.9, 132.6, 128.5, 128.3, 128.1, 128.1, 128.0, 127.9, 127.4, 126.3, 126.3, 117.8, 115.7, 80.3, 78.0, 71.9, 63.1, 62.7, 53.7, 46.0, 36.3, 7.8 ppm

EXAMPLE 10

Synthesis of (R)-3-(3-benzyloxymethyl-2-methoxy-pyridin-4-yl)-3-hydroxy-pentanoic acid 4.733 g (4R,5S)-3-acetyl-4,5-diphenyl-oxazolidin-2-one (16.82 mmol, 1.2 eq) as obtainable from Example 8, were dissolved in 19 mL THF at 65° C. The solution was subsequently cooled to −78° C. and 17.00 mL lithium bis(trimethylsilyl)amide solution in TBF (1.0 M, 16.82 mmol, 1.2 eq) were slowly added (addition time: 10 min). During the addition, the color changed from colorless to bright yellow. After 2 h at −78° C., the clear solution was cooled to −95° C. A solution of 4.000 g 1-(3-benzyloxymethyl-2-methoxy-pyridin-4-yl)-propan-1-one (14.02 mmol) as obtainable from Example 7, in 16 mL THF was slowly added (syringe pump, addition time: 30 min) and the solution was kept for additional 30 min at −95° C. and then for 45 min at −78° C. Subsequently, 87.6 mL aqueous LiOH solution (0.8 M, 70.1 mmol, 5.0 eq) and 7.01 mL aqueous H$_2$O$_2$ solution (10.0 M, 70.1 mmol, 5.0 eq) were added and stirring of the resulting suspension was continued at 0° C. for 30 min and at room temperature for 1 h. The precipitated auxiliary was collected by filtration and the solid was washed with 15 mL water. The filtrate was poured on 200 mL aqueous NaOH solution (2 M). A second portion of precipitated auxiliary was collected by filtration and the solid was washed with 3 mL water. The filtrate was then extracted 3 times with 200 mL, in total with 600 mL TBME in order to remove unreacted 1-(3-benzyloxymethyl-2-methoxy-pyridin-4-yl)-propan-1-one, unprecipitated auxiliary and several impurities. The aqueous phase was then acidified with aqueous HCl until pH 3. The resulting white suspension was extracted twice with 200 mL, in total 400 mL dichloromethane. The combined dichloromethane extracts were washed with 80 mL saturated aqueous NH$_4$Cl and 16 mL brine and were subsequently dried over 20 g sodium sulfate (30 min) and filtered. The solid was washed with 40 mL dichloromethane. After removal of solvent in a rotary evaporator (40° C., 5 mbar), the title compound was obtained as a light yellow oil (3.61 g, 75% by weight, er 87.2:12.8).

$[\alpha]_D^{20}$ (c=0.9884 g/dL, CHCl$_3$)=−23.3 (for ee=100%);
$^1$H NMR (300 MHz, CDCl$_3$): δ 8.08 (d, 1H, J=5.5 Hz), 7.35 (m, 5H), 6.78 (d, 1H, J=5.5 Hz), 6.16 (s, 1H), 4.97 (d, 1H, J=11.3 Hz), 4.86 (d, 1H, J=11.3 Hz), 4.65 (d, 1H, J=11.7 Hz), 4.60 (d, 1H, J=11.7 Hz), 3.93 (s, 3H), 2.96 (d, 1H, J=15.5 Hz), 2.84 (d, 1H, J=16.1 Hz), 1.86 (m, 2H), 0.76 (t, 3H, J=7.5 Hz) ppm;
$^{13}$C NMR (100 MHz, CDCl$_3$): δ 173.7, 163.5, 155.3, 146.4, 137.2, 128.5, 128.4, 128.1, 128.1, 117.1, 115.7, 72.8, 63.2, 54.0, 46.3, 35.8, 7.9 ppm

EXAMPLE 11

Synthesis of (R)-5-ethyl-5-hydroxy-2,5,6,9-tetrahydro-8-oxa-2-aza-benzocycloheptene To a stirred solution of 3.00 g (R)-3-(3-benzyloxymethyl-2-methoxy-pyridin-4-yl)-3-hydroxy-pentanoic acid (8.69 mmol), as obtainable from Example 10, in 11 mL 1,2-dimethoxyethane, were added 2.01 mL aqueous HBr (48%) (17.89 mmol, 2.06 eq). After 15 min at room temperature, the solution was heated to 50° C. After 4 h, the first product crystals appeared. The reaction was monitored by HPLC. After 24 h at 50° C. (<1% area (R)-3-(3-benzyloxymethyl-2-methoxy-pyridin-4-yl)-3-hydroxy-pentanoic acid), the reaction was cooled to room temperature. The mixture was allowed to stir at room temperature for 72 h and was then filtered. The solid was washed twice with 2.24 mL, in total with 4.48 mL TBME, and subsequently with 2.24 mL acetone; twice with 2.24 mL, in total with 4.48 mL water, and finally twice with 2.24 mL, in total with 4.48 mL acetone. After drying in vacuo, the title compound (1.040 g, 4.66 mmol, 54% by weight) was obtained as white crystals, and in an enantiomeric ratio of er=99.95:0.05 as determined by the following Chiral HPLC method:

| | |
|---|---|
| Method | 750DH2.M |
| Sample preparation | ethanol solution |
| Equipment | Agilent 1100 |
| Column | Chiralcel-ODH, 250 x 4.6, Nr. DB075 |
| Temperature | 25° C. |
| Mobile phase | 75% heptane, 25% ethanol/trifluoroacetic acid (99:1) |
| Flow | 0.8 mL/min |
| Injection volume | 5 µL |
| Detection | UV 308 nm |
| Retention time | 9.68 min(S)-product; 13.28 min(R)-product |

Mp >270° C. (decomposition);
$[\alpha]_D^{20}$ (c=1.1000 g/dL, DMSO)=+134.4;
$^1$H NMR (300 MHz, DMSO): δ 11.67 (br. s, 1H), 7.34 (d, 1H, 7.2 Hz), 6.33 (d, 1H, 7.2 Hz), 5.72 (br. s, 1H), 5.34 (d, 1H, J=15.1 Hz), 5.21 (d, 1H, J=15.1 Hz), 3.32 (d, 1H, J=13.5 Hz), 2.98 (d, 1H, J=13.7 Hz), 1.68 (m, 2H), 0.80 (t, 3H, J=7.5 Hz) ppm;
$^{13}$C NMR (100 MHz, DMSO): δ 171.9, 161.1, 155.6, 133.7, 122.6, 104.9, 72.7, 61.0, 42.2, 35.7, 8.1 ppm

EXAMPLE 12

Synthesis of 2-chloro-N-isopropyl-isonicotinamide

To a stirred suspension of 20.00 g 2-chloroisonicotinic acid (123.2 mmol) in 200 mL acetonitrile were added 11.77 mL thionyl chloride (160.2 mmol, 1.3 eq) and 762 µL DMF (9.86 mmol, 0.08 eq). The mixture was heated to reflux and was monitored by HPLC. After 60 min (<1% of 2-chloroisonicotinic acid), the reaction mixture was cooled to room temperature and all volatiles were removed in a rotary evaporator (40° C./10 mbar). The residual oil was dissolved in 200 mL dichloromethane and the solution was cooled to 0° C. 20.6 mL triethylamine (147.8 mmol, 1.20 eq) and 11.7 mL isopropylamine (135.5 mmol, 1.10 eq) were subsequently added and stirring was continued for 2 h at 0° C. until the solution turned almost black. The mixture was poured on 200 mL water and phases were separated. The organic phase was washed with 200 mL brine, dried over 15 g sodium sulfate and filtered. The filter cake was washed with 30 mL dichloromethane. After removal of solvent in a rotary evaporator (40° C., 20 mbar), the crude product (24.83 g, 102% w/w) was obtained as a brown solid (HPLC purity 98.6% area).

Mp: 99° C. (decomp.);
$^1$H NMR (300 MHz, CDCl$_3$): δ 8.50 (dd, 1H, J=4.9 Hz, J=0.6 Hz), 7.62 (dd, 1H, J=1.3 Hz, J=0.6 Hz), 7.51 (dd, 1H, J=5.1 Hz, J=1.5 Hz), 5.94 (br. s, 1H), 4.27 (m, 1H), 1.28 (d, 6H, J=6.6 Hz) ppm;
$^{13}$C NMR (100 MHz, CDCl$_3$): δ 163.4, 152.4, 150.4, 145.1, 122.0, 119.8, 42.5, 22.6 ppm.

EXAMPLE 13

Synthesis of N-isopropyl-2-methoxy-isonicotinamide

To a stirred solution of 19.44 g 2-chloro-N-isopropyl-isonicotinamide (97.86 mmol) as obtainable from example 12, in 165 mL methanol were added 27.82 g NaOMe (489.3 mmol, 5.0 eq) in four equal portions over 60 min. The solution was then heated to 80° C. and the reaction was monitored by HPLC. After 23 h (<2% area starting material 2-chloro-N-isopropyl-isonicotinamide), the mixture was cooled to room temperature and quenched by addition of 200 mL saturated aqueous NH$_4$Cl. The product was extracted three times with 150 mL, in total 450 mL dichloromethane. The combined organic phases were dried over 40 g Na$_2$SO$_4$ (30 min) and filtered. The filter cake was washed with 80 mL dichloromethane. After removal of solvent in a rotary evaporator (40° C., 22 mbar), the crude product (15.856 g, 83% w/w, HPLC purity 93.7% area) was obtained as a white solid.

Mp: 100° C.
$^1$H NMR (300 MHz, CDCl$_3$): δ 8.24 (dd, 1H, J=5.3 Hz, J=0.6 Hz), 7.15 (dd, 1H, J=5.3 Hz, J=1.3 Hz), 7.02 (dd, 1H, J=1.3 Hz, J=0.6 Hz), 5.89 (br. s, 1H), 4.28 (m, 1m), 3.96 (s, 3H), 1.26 (d, 6H, J=6.6 Hz) ppm;
$^{13}$C NMR (100 MHz, CDCl$_3$): δ 165.34, 165.26, 148.3, 145.6, 114.5, 109.1, 54.3, 42.7, 23.2 ppm.

EXAMPLE 14

Synthesis of 3-hydroxy-2-isopropyl-4-methoxy-2,3-dihydro-pyrrolo[3,4-c]pyridin-1-one To a stirred suspension of 10.00 g N-isopropyl-2-methoxy-isonicotinamide (51.40 mmol), as obtainable from example 13, in 300 mL TBME were added at room temperature 17.2 mL TMEDA (113.3 mmol, 2.2 eq) resulting in the formation of a clear solution, which was then cooled to –780 C. Subsequently 102.8 mL n-butyllithium in hexane (1.5 M, 154.4 mmol, 3.0 eq) were then added over 35 min and stirring was continued at the same temperature for additional 3 h min and subsequently at –22° C. for another 3 h. To the slightly brown suspension, 13.9 mL DMF (180.0 mmol, 3.5 eq) were added at –28° C. The resulting suspension was quenched after 16 h 45 min by addition of 200 mL saturated aqueous NH$_4$Cl. The mixture was extracted three times with 150 mL, in total 450 mL dichloromethane. The combined organic phases were dried over 20 g Na$_2$SO$_4$ (30 min) and filtered. The filter cake was washed with 40 mL dichloromethane. After evaporation of solvent in a rotary evaporator (40° C./20 mbar), the crude product (19.400 g, 170% w/w, regioselectivity: 11.68:1, as determined by $^1$H-NMR) was obtained as a brown oil (HPLC purity 77.6%).

Mp 117° C.;
$^1$H NMR (300 MHz, CDCl$_3$): δ 8.33 (d, 1H, J=5.1 Hz), 7.26 (dd, 1H, J=5.1 Hz), 6.05 (d, 1H, J=7.5 Hz), 4.40 (sept, 1H, J=6.8 Hz), 4.07 (s, 3H), 2.44 (d, 1H, J=8.5 Hz), 1.44 (d, 3H, J=6.8 Hz), 1.42 (d, 3H, J=6.8 Hz) ppm;
$^{13}$C NMR (100 MHz CDCl$_3$): δ 165.3, 159.3, 149.2, 143.1, 124.6, 110.8, 79.9, 53.9, 44.4, 21.8, 20.1 ppm.

EXAMPLE 15

Synthesis of 4-methoxy-3H-furo[3,4-c]pyridin-1-one

To a stirred solution of 19.40 g crude 3-hydroxy-2-isopropyl-4-methoxy-2,3-dihydro-pyrrolo[3,4-c]pyridin-1-one (87.29 mmol), as obtainable from example 14, in 300 mL isopropanol and 100 mL water were added at room temperature 5.160 g NaBH$_4$ (130.9 mmol, 1.5 eq). After 3 h (<1.0% area 3-hydroxy-2-isopropyl-4-methoxy-2,3-dihydro-pyrrolo[3,4-c]pyridin-1-one), the reduction was quenched at 0° C. by addition of 34.0 mL acetone (474.4 mmol, 5.3 eq) and stirring was continued for 35 min at room temperature. The mixture was poured on 415 mL aqueous HCl (2.0 M, 829.3 mmol, 9.5 eq) at 0° C. and stirring was continued for 20 min at room temperature. The mixture was then heated to 50° C. overnight and was subsequently cooled to 0° C. Dipotassium hydrogen phosphate was added in order to adjust pH 3.0 and ca. 95% of the isopropanol were removed in a rotary evaporator (40° C./10 mbar). Water was added until the salts were dissolved and the mixture was extracted three times with 300 mL, in total 900 mL dichloromethane. The combined organic phases were dried over 50 g Na$_2$SO$_4$ (30 min) and filtered. The solid was washed with 100 mL dichloromethane. After evaporation of solvent in a rotary evaporator (40° C./25 mbar), the crude product (9.963 g, 69% w/w) was obtained as a light brown solid (HPLC purity 80.7% area). Purification was achieved by trituration with 30 mL ethyl acetate for 24 h at room temperature and subsequent addition of 60 mL heptane. The suspension was then allowed to stand for 24 h at 5° C. yielding the title product (5.486 g, 33.22 mmol, 40% w/w (68% over 2 steps), HPLC purity 95.1% area) as a beige solid.

Mp: 90° C.;
$^1$H NMR (300 MHz CDCl$_3$): δ 8.35 (d, 1H, J=5.1 Hz), 7.36 (d, 1H, J=5.3), 5.29 (s, 2H), 4.07 (s, 3H) ppm;
$^{13}$C NMR (100 MHz, CDCl$_3$): δ 169.6, 159.3, 148.1, 136.3, 129.0, 111.7, 68.1, 54.0 ppm.

EXAMPLE 16

Synthesis of 1-ethyl-4-methoxy-1,3-dihydro-furo[3,4-c]pyridin-1-ol

To 10.52 mL triethylaluminum in toluene (1.9 M, 19.99 mmol, 1.1 eq) were added dropwise 39.97 mL ethyllithium in cyclohexane/benzene (0.5 M, 19.99 mmol, 1.1 eq) at 0° C. After 15 min at 0° C., 50.5 mL THF (precooled to –40° C.), were added rapidly via a canula. A solution of 3.0 g 4-methoxy-3H-furo[3,4-c]pyridin-1-one (18.17 mmol), as obtainable from example 15, in 75 mL THF was subsequently added rapidly at 40° C. After 10 min at –40° C., additional 39.97 mL ethyllithium in cyclohexane/benzene (0.5 M, 19.99 mmol, 1.1 eq) were added slowly. The mixture was allowed to warm up to –15° C. within 3 h and the reaction was afterwards quenched by addition of 3.68 mL methanol (100 mmol, 5 eq). After 30 min, the mixture was poured in 1.5 L saturated aqueous potassium sodium tartrate and was extracted three times with 500 mL, in total with 1.5 L dichloromethane. The combined organic phases were dried over 100 g Na$_2$SO$_4$ (30 min) and filtered. The solid was washed with 200 mL dichloromethane. After evaporation of solvent in a rotary evaporator (40° C./10 mbar), the crude product (3.77 g, 106% w/w) was obtained as a brown oil (HPLC purity 51.5% area), which was purified by column chromatography with heptane/ethyl acetate (7:3) yielding the title product (1.877 g, 9.61 mmol, 53% w/w ; HPLC purity 97.9% area; ratio lactol/hydroxy-ketone=6:1 by NMR) as yellow oil.

Mp: 145° C.

$^1$H NMR (300 MHz, CDCl$_3$): lactol-form: δ 8.15 (d, 1H, J=5.3 Hz), 6.90 (d, 1H, J=5.2 Hz), 5.13 (d, 1H, J=13.2 Hz), 4.95 (d, 1H, J=13.2 Hz), 3.99 (s, 3H), 2.86 (s, 1H), 2.06 (m, 2H), 0.86 (t, 3H, J=7.4 Hz) ppm;

hydroxy-ketone-form: δ 8.21 (d, 1H, J=5.3 Hz), 6.99 (d, 1H, J=5.2 Hz), 4.63 (d, 2H, J=7.2 Hz), 4.00 (s, 3H), 3.07 (t, 1H, J=7.1 Hz), 2.92 (q, 2H, J=7.1 Hz), 1.21 (t, 3H, J=7.1 Hz) ppm;

$^{13}$C NMR (100 MHz, CDCl$_3$): lactol-form: δ 159.9, 151.9, 146.9, 121.6, 110.7, 110.6, 69.4, 53.5, 32.2, 8.0 ppm.

EXAMPLE 17

Synthesis of 1-[3-(tert-Butyl-dimethyl-silanyloxymethyl)-2-methoxy-pyridin-4-yl]-propan-1-one To a solution of 1.500 g 1-ethyl-4-methoxy-1,3-dihydro-furo[3,4-c]pyridin-1-ol (7.68 mmol) as obtainable from example 16, and 1.831 g imidazole (26.89 mmol, 3.5 eq) in 12.5 mL DMF were added 3.475 g TBSCl (23.05 mmol, 3.0 eq) at 0° C. The solution was allowed to slowly warm up to room temperature overnight until less than 0.1% area 1-ethyl-4-methoxy-1,3-dihydro-furo[3,4-c]pyridin-1-ol were achieved, as detected by HPLC. 285 mL heptane and 444 mL water were added. The organic phase was separated, dried over 20 g Na$_2$SO$_4$ (30 min) and filtered. The solid was washed with 40 mL heptane.

After evaporation in a rotary evaporator (40° C./10 mbar) and subsequently under high vacuum (40° C., 0.01 mbar), the title product (2.34 g, 7.56 mmol, 98% w/w) was obtained as a light yellow oil (HPLC purity 99.0% area).

$^1$H NMR (300 MHz, CDCl$_3$): δ 8.11 (d, 1H, J=5.1 Hz), 6.72 (d, 1H, J=5.2 Hz), 4.77 (s, 2H), 3.96 (s, 3H), 2.82 (t, 2H, J=7.1 Hz), 1.16 (t, 3H, J=7.2 Hz), 0.88 (s, 3H), 0.00 (s, 3H) ppm;

$^{13}$C NMR (100 MHz, CDCl$_3$): δ 205.1, 160.2, 149.2, 144.8, 118.6, 112.9, 56.3, 52.7, 35.4, 24.9, 17.6, 6.7, −6.6 ppm.

EXAMPLE 18

Synthesis of (R)-3-{3-[3-(tert-butyl-dimethyl-silanyloxymethyl)-2-methoxy-pyridin-4-yl]-3-hydroxy-pentanoyl}-4-phenyl-oxazolidin-2-one A suitable reaction flask was charged with 9.79 mL lithium bis(trimethylsilyl)amide solution (1.0 M in THF, 9.69 mmol, 3.0 eq) and the solution was cooled to −78° C. 1.989 g (R)-3-acetyl-4-phenyl-oxazolidin-2-one (9.69 mmol, 3.0 eq), as obtainable from example 21, in 7.5 mL THF were slowly added (ca. 10 min). After 2 h at −78° C., the solution was cooled to −95° C. and 1.000 g 1-[3-(tert-Butyl-dimethyl-silanyloxymethyl)-2-methoxy-pyridin-4-yl]-propan-1-one (3.231 mmol), as obtainable from example 17, dissolved in 6.7 mL THF were slowly added (ca. 60 min) using a syringe pump. The solution was kept for additional 30 min at −95° C. and then for 1 h at −78° C. Subsequently, the reaction was quenched by addition of 50 mL aqueous 0.5 M HCl. The mixture was extracted three times with 50 mL, in total 150 mL dichloromethane and the combined extracts were dried over 10 g Na$_2$SO$_4$ (30 min) and filtered. The filter cake was washed with 20 mL dichloromethane. After removal of solvent in a rotary evaporator (40° C., 5 mbar), the crude product was obtained as an orange solid (3.12 g, 188% w/w, dr=87:13 (calculated by $^1$H-NMR), HPLC purity 37.8% area). An analytical sample (dr>50:1; HPLC purity 100% area, colorless oil) was obtained by semipreparative HPLC.

$[\alpha]_D^{20}$ (c=0.285 g/dL, CHCl$_3$)=−98.1;

$^1$H NMR (300 MHz, CDCl$_3$): δ 7.90 (d, 1H, J=5.4 Hz), 7.23 (m, 3H), 7.03 (m, 2H), 6.67 (d, 1H, J=5.5 Hz), 5.42 (s, 1H), 5.35 (dd, 1H, J=8.7 Hz, J=4.0 Hz), 4.97 (d, 1H, J=11.6 Hz), 4.93 (d, 1H, J=11.6 Hz), 4.62 (t, 1H, J=8.7 Hz), 4.18 (dd, 1H, J=8.6 Hz, J=4.2 Hz), 4.07 (d, 1H, J=16.2 Hz), 3.91 (s, 3H), 3.23 (d, 1H, J=16.2 Hz), 1.90 (m, 2H), 0.87 (s, 9H), 0.78 (t, 3H, J=7.4 Hz), 0.06 (s, 3H), 0.01 (s, 3H) ppm;

$^{13}$C NMR (100 MHz, CDCl$_3$): δ 170.6, 162.8, 155.4, 153.7, 145.3, 138.4, 129.0, 128.4, 125.4, 120.3, 115.5, 78.1, 69.8, 57.5, 56.5, 53.5, 46.0, 36.4, 25.9, 18.3, 7.9, −5.3, −5.4 ppm.

EXAMPLE 19

Synthesis of (R)-3-hydroxy-3-(3-hydroxymethyl-2-methoxy-pyridin-4-yl)-pentanoic acid To a solution of 3.11 g (R)-3-{3-[3-(tert-butyl-dimethyl-silanyloxymethyl)-2-methoxy-pyridin-4-yl]-3-hydroxy-pentanoyl}-4-phenyl-oxazolidin-2-one (6.04 mmol), as obtainable from example 18, in 35 mL THF were added at 0° C. 37.8 mL aqueous LiOH solution (0.8 M, 30.2 mmol, 5.0 eq) and 3.02 mL aqueous H$_2$O$_2$ solution (10.0 M, 30.2 mmol, 5.0 eq). After 30 min, 220 mL aqueous NaOH solution (2 M) were added and the ice bath was removed. The reaction was monitored by HPLC. After 2 h (<0.2% area (R)-3-{3-[3-(tert-butyl-dimethyl-silanyloxymethyl)-2-methoxy-pyridin-4-yl]-3-hydroxy-pentanoyl}-4-phenyl-oxazolidin-2-one), the resulting emulsion was extracted 7 times with 100 mL, in total 700 mL TBME. The aqueous phase was acidified with aqueous HCl in order to adjust pH 3.0 and extracted nine times with 100 mL, in total 900 mL dichloromethane/ethanol (4:1). After evaporation in a rotary evaporator (40° C., 5 mbar), the title product was obtained as a colorless semisolid (700 mg, 2.74 mmol, yield of 45% w/w, or 85% when calculated over the two steps) and in a purity of 89.2% as determined by HPLC (er=80.47:19.53, see Chiral HPLC method below).

| Chiral HPLC method | |
|---|---|
| Method | 90ADH1.M |
| Sample preparation | ethanol solution |
| Equipment | Agilent 1100 |
| Column | Chiralpak-ADH, 250x4.6, Nr. DB078 |
| Temperature | 25° C. |
| Mobile phase | 90 % heptane, 10 % ethanol/trifluoroacetic acid (99:1) |
| Flow | 0.8 mL/min |
| Injection volume | 5 µL |
| Detection | UV 308 nm |

Retention time: 22.20 min for (R)-3-{3-[3-(tert-butyl-dimethyl-silanyloxymethyl)-2-methoxy-pyridin-4-yl]-3-hydroxy-pentanoyl}-4-phenyl-oxazolidin-2-one ; and 24.78 min for (S)-3-{3-[3-(tert-butyl-dimethyl-silanyloxymethyl)-2-methoxy-pyridin-4-yl]-3-hydroxy-pentanoyl}-4-phenyl-oxazolidin-2-one.

$[\alpha]_D^{20}$ (c=1.3154 g/dL, CHCl$_3$)=+9.1;

$^1$H NMR (300 MHz, CDCl$_3$): δ 8.03 (d, 1H, J=5.5 Hz), 6.76 (d, 1H, J=5.4 Hz), 5.04 (d, 1H, J=12.2 Hz), 4.89 (d, 1H,

J=12.2 Hz), 3.97 (s, 3H), 3.07 (d, 1H, J=16.2 Hz), 2.85 (d, 1H, J=16.2 Hz), 1.92 (br. q, 2H, J=7.5), 0.82 (t, 3H, J=7.4 Hz) ppm;

$^{13}$C NMR (100 MHz, CDCl$_3$): δ 175.6, 163.5, 154.2, 145.5, 120.9, 115.3, 77.4, 56.5, 54.1, 44.7, 35.3, 8.1 ppm.

EXAMPLE 20

Synthesis of (R)-5-ethyl-5-hydroxy-2,5,6,9-tetrahydro-8-oxa-2-aza-benzocycloheptene To a stirred solution of 1.097 g (R)-3-hydroxy-3-(3-hydroxymethyl-2-methoxy-pyridin-4-yl)-pentanoic acid (4.298 mmol) as obtainable from example 19, in 15.1 mL 1,2-dimethoxyethane, were added 1.014 mL aqueous HBr (48%) (9.03 mmol, 2.1 eq). After 15 min at room temperature, the solution was heated to 50° C. After 18 h at 50° C., the resulting suspension was allowed to stir at room temperature for additional 24 h and subsequently to stand at 5° C. for 18 h. The precipitate was collected by filtration using no vacuum and was subsequently washed twice with 2.55 mL, in total with 5.1 mL TBME, then with 2.55 mL acetone, two times with 3.18 mL, in total with 6.36 mL water and finally two times with 3.18 mL, in total with 6.36 mL acetone. After evaporation of residual solvent in a rotary evaporator (40° C./10 mbar), the title compound was obtained as white crystals (418.1 mg, 1.873 mmol, 44% w/w), in high purity (HPLC purity 100% area), and in an enantiomeric ratio of er=100.00:0.00 (see chiral HPLC method below).

| Chiral HPLC method | |
|---|---|
| Method | 750DH2.M |
| Sample preparation | ethanol solution |
| Equipment | Agilent 1100 |
| Column | Chiralcel-ODH, 25 0x4.6, Nr. DB075 |
| Temperature | 25° C. |
| Mobile phase | 75% heptane, 25% ethanol/trifluoroacetic acid (99:1) |
| Flow | 0.8 mL/min |
| Injection volume | 5 μL |
| Detection | UV 308 nm |

Retention time: 9.68 min for (S)-5-ethyl-5-hydroxy-2,5,6,9-tetrahydro-8-oxa-2-aza-benzocycloheptene; and 13.28 min for (R)-5-ethyl-5-hydroxy-2,5,6,9-tetrahydro-8-oxa-2-aza-benzocycloheptene.

$[α]_D^{20}$ (c=1.178 g/dL, DMSO)=+127.9;

Mp >270° C. (decomp.);

$^1$H NMR (300 MHz, DMSO): δ 11.67 (br. s, 1H), 7.34 (d, 1H, 7.2 Hz), 6.33 (d, 1H, 7.2 Hz), 5.72 (br. S, 1H), 5.34 (d, 1H, J=15.1 Hz), 5.21 (d, 1H, J=15.1 Hz), 3.32 (d, 1H, J=13.5 Hz), 2.98 (d, 1H, J=13.7 Hz), 1.68 (m, 2H), 0.80 (t, 3H, J=7.5Hz) ppm;

all other analytical data are in accordance with those described in example 11.

EXAMPLE 21

Synthesis of (R)-3-acetyl-4-phenyl-oxazolidin-2-one

To a stirred suspension of 5.000 g (4R)-(-)-4-phenyl-2-oxazolidinone (30.03 mmol) in 100 mL THF, were added 21.0 mL n-butyllithium in hexane (1.5 M, 31.53 mmol, 1.05 eq) at 0° C. within 10 min. The resulting colorless solution was stirred for additional 50 min at 0° C. 2.57 mL acetyl chloride (36.04 mmol, 1.2 eq) were then added within 1 min. After 3.5 h the reaction was stopped by addition of 25 mL saturated aqueous NH$_4$Cl and the mixture was extracted with 75 mL ethyl acetate. The organic phase was washed with 50 mL saturated aqueous NaHCO$_3$ and with 50 mL brine. The solution was dried for 30 minutes over 5 g Na$_2$SO$_4$ and filtered. The filter cake was washed with 10 mL ethyl acetate. After removal of solvent in a rotary evaporator (40° C., 18 mbar), the crude product was obtained as white crystals (6.13 g, 100% w/w; HPLC purity 88.3% area). Further purification was achieved by dissolving in 10.6 mL ethyl acetate at reflux temperature and subsequent dropwise addition of 26.6 mL heptane. The resulting suspension was allowed to slowly cool down to 5° C. and after standing overnight, the precipitate was collected by filtration. After washing with 3 mL heptane, the title compound was obtained as white crystals (5.26 g, 25.6 mmol, 85% by weight) and in high purity (HPLC purity 96.6% area).

$[α]_D^{20}$ (c=0.083 g/dL, CHCl$_3$)=-58.8;

Mp: 94° C.;

$^1$H NMR (300 MHz CDCl$_3$): δ 7.25-7.42 (m, 5H), 5.42 (dd, 1H, J=8.8 Hz, J=3.5 Hz), 4.69 (t, 1H, J=8.8 Hz), 4.29 (dd, 1H, J=8.8 Hz, J=3.5 Hz), 2.53 (s, 3H) ppm;

$^{13}$C NMR (100 MHz, CDCl$_3$): δ 169.7, 153.9, 139.1, 129.2, 128.8, 126.0, 70.0, 57.5, 23.8 ppm.

The invention claimed is:

1. A process for the production of compounds of formula (I)

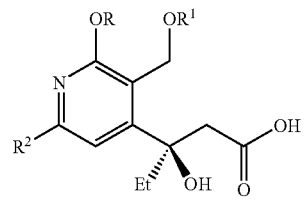

and pharmaceutically acceptable salts and esters thereof, comprising a) reacting a compound of formula (II),

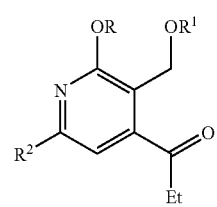

with a compound of formula (III),

and b) further reacting in the presence of alkali- or earth alkali metal hydroxides to give the compounds of formula (I), wherein
R and R¹ are independently, alkyl or benzyl, which benzyl is optionally substituted by one, two or three substituents including —O-alkyl; alkyl or halogen; with the proviso that:
if R is alkyl, R¹ in formula (I) may also be hydrogen or silyl, and R¹ in formula (II) may also be silyl;
R² is hydrogen or halogen;
X is

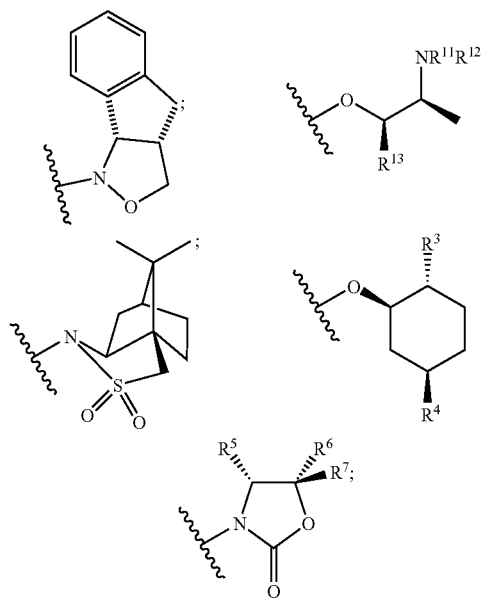

R³ and R⁴ are hydrogen, phenyl, alkyl or —C(CH₃)₂-phenyl;
R⁵ is phenyl, benzyl or alkyl;
R⁶ is hydrogen, alkyl or phenyl; and
R⁷ is hydrogen, methyl or phenyl; or alternatively
R⁵ and R⁶, together with the carbon atoms to which they are attached form an indan moiety and R⁷ is hydrogen;
R¹¹ and R¹² air independently alkyl, cycloalkyl, benzyl or phenyl; and
R¹³ is phenyl or alkyl.

2. The process according to claim 1 comprising
a) reacting a compound of formula (II),

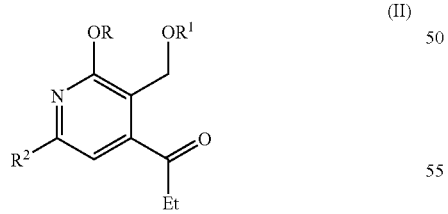

with a compound of formula (III),

and
b) further reacting in the presence of alkali- or earth alkali metal hydroxides to give the compounds of formula (I), wherein
R and R¹ are independently alkyl or benzyl, which benzyl is optionally substituted by one, two or three substituents including —O-alkyl; alkyl or halogen;
R² is hydrogen or halogen;
X is

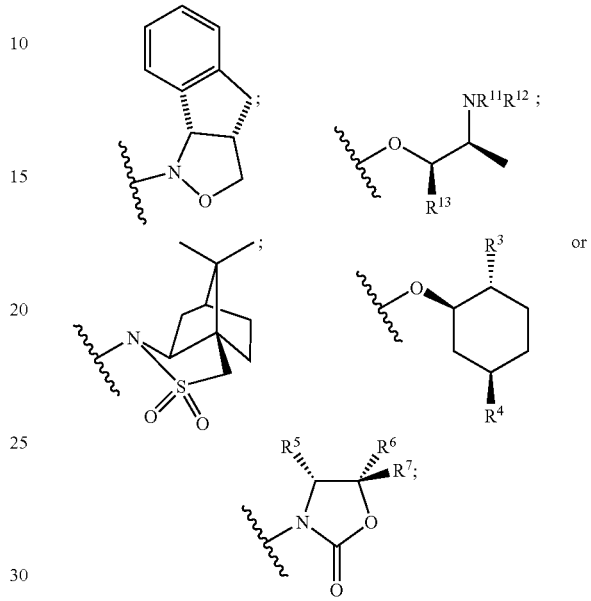

R³ and R⁴ are hydrogen, phenyl, alkyl or —C(CH₃)₂-phenyl;
R⁵ is phenyl, benzyl or alkyl;
R⁶ is hydrogen, alkyl or phenyl; and
R⁷ is hydrogen, methyl or phenyl; or alternatively
R⁵ and R⁶, together with the carbon atoms to which they am attached form an indan moiety and R⁷ is hydrogen;
R¹¹ and R¹² are independently alkyl, cycloalkyl, benzyl or phenyl; and
R¹³ is phenyl or alkyl.

3. A process according to claim 1, comprising
a) reacting a compound of formula (II),

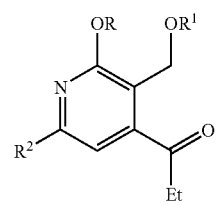

with a compound of formula (III),

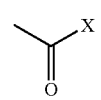

and
b) further reacting in the presence of alkali- or earth alkali metal hydroxides to give the compound of formula (I), wherein R is alkyl; and R¹ is hydrogen or silyl in formula (I) and silyl in formula (II);

R² is hydrogen or halogen:

X is

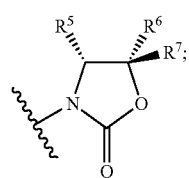

R⁵ is phenyl, benzyl or alkyl;

R⁶ is hydrogen, alkyl or phenyl; and

R⁷ is hydrogen, methyl or phenyl.

4. The process according to claim 1 or 2, wherein X is

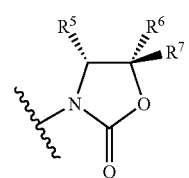

wherein

R⁵ is phenyl, benzyl, isopropyl, tert-butyl or methyl;

R⁶ is hydrogen, methyl or phenyl; and

R⁷ is hydrogen, methyl or phenyl; or alternatively

R⁵ and R⁶ together with the carbon atoms to which they are attached, form an indan moiety and R⁷ is hydrogen.

5. The process according to claim 4, wherein

R⁵ and R⁶ are both phenyl, and

R⁷ is hydrogen.

6. The process according to claim 1 or 2, wherein the compound of formula (I-1)

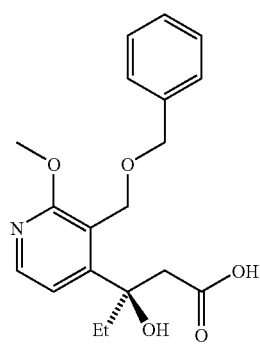

is obtained by a) reacting the compound of formula (II-1)

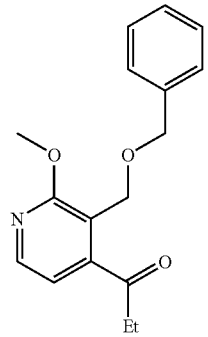

with the compound formula (III-1)

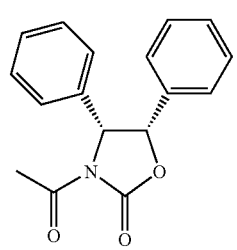

b) further reacting in the presence of lithium hydroxide in combination with hydrogen peroxide, to give the corresponding compound of formula (I).

7. The process according to claim 1, wherein the compound of formula (I-2)

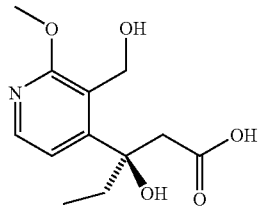

is obtained by a) reacting the compound of formula (II-2)

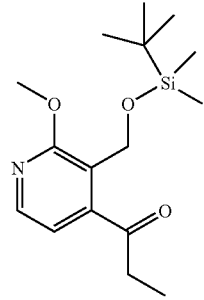

with the compound of formula (III-2)

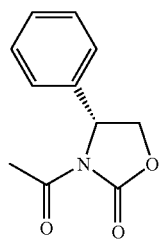

b) further reacting in the presence of lithium hydroxide in combination with hydrogen peroxide, to give the corresponding compound of formula (I-2).

8. The process of claim 1, whereby the process step a) is carried out in the presence of an alkali- or earth-alkali metal amide base.

9. The process of claim 1, whereby the process step a) is carried out in the presence of lithium hexamethyldisilazane (LHMDS).

10. The process of claim 1, whereby the process step a) is carried out in a solvent including diethylether ($Et_2O$), tetrahydrofuran (THF), tert-butyl methyl ether (TBME), pentane, hexane or heptane.

11. The process according to claim 10, whereby the solvent of process step a) is tetrahydrofuran (THF).

12. The process of claim 1, whereby the process step a) is carried out at temperatures between 25° C. and −120° C.

13. The process according to claim 12, whereby the process step a) is carried out at temperatures between −60° C. and −100° C.

14. The process according to claim 12, whereby the process step a) is carried out at temperatures between −90° C. and 100° C.

15. The process of claim 1, whereby the process step b) is carried out in the presence of an alkali- or earth alkali metal hydroxide, alone or in combination with hydrogen peroxide.

16. The process according to claim 15, whereby the process step b) is carried out in the presence of lithium hydroxide in combination with hydrogen peroxide.

17. The process according to claim 1 or 2, wherein X is

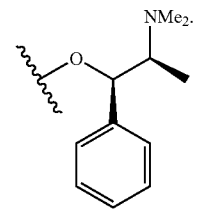

* * * * *